United States Patent
Wang et al.

(10) Patent No.: US 7,413,565 B2
(45) Date of Patent: Aug. 19, 2008

(54) MINIMALLY INVASIVE SURGICAL TRAINING USING ROBOTICS AND TELECOLLABORATION

(75) Inventors: Yulun Wang, Goleta, CA (US); Modjtaba Ghodoussi, Santa Barbara, CA (US); Darrin Uecker, Santa Barbara, CA (US); James Wright, Santa Barbara, CA (US); Amante Mangaser, Goleta, CA (US); Ranjan Mukherjee, East Lansing, MI (US)

(73) Assignee: Intuitive Surgical, Inc., Sunnyvale, CA (US)

( * ) Notice: Subject to any disclaimer, the term of this patent is extended or adjusted under 35 U.S.C. 154(b) by 579 days.

(21) Appl. No.: 10/948,853

(22) Filed: Sep. 23, 2004

(65) Prior Publication Data

US 2005/0038416 A1      Feb. 17, 2005

Related U.S. Application Data

(62) Division of application No. 10/246,236, filed on Sep. 17, 2002, now Pat. No. 6,951,535.

(51) Int. Cl.
*A61B 17/00* (2006.01)
*G06F 19/00* (2006.01)

(52) U.S. Cl. ................................. 606/1; 700/245; 901/3

(58) Field of Classification Search .................. 600/101, 600/102; 700/245, 258, 65–66; 901/9, 3, 901/6, 8, 41, 48; 606/1, 130
See application file for complete search history.

(56) References Cited

U.S. PATENT DOCUMENTS

| | | | |
|---|---|---|---|
| 977,825 A | 12/1910 | Murphy | |
| 3,171,549 A | 3/1965 | Orloff | |
| 3,280,991 A | 10/1966 | Melton et al. | |

(Continued)

FOREIGN PATENT DOCUMENTS

DE      9204118      7/1992

(Continued)

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

(Continued)

*Primary Examiner*—Linda C. M. Dvorak
*Assistant Examiner*—Alireza Nia

(57) ABSTRACT

A medical system that allows a mentor to teach a pupil how to use a robotically controlled medical instrument. The system may include a first handle that can be controlled by a mentor to move the medical instrument. The system may further have a second handle that can be moved by a pupil to control the same instrument. Deviations between movement of the handles by the mentor and the pupil can be provided as force feedback to the pupil and mentor handles. The force feedback pushes the pupil's hand to correspond with the mentor's handle movement. The force feedback will also push the mentor's hand to provide information to the mentor on pupil's movements. The mentor is thus able to guide the pupil's hands through force feedback of the pupil handles to teach the pupil how to use the system.

10 Claims, 13 Drawing Sheets

U.S. PATENT DOCUMENTS

| | | | |
|---|---|---|---|
| 4,058,001 A | 11/1977 | Waxman | |
| 4,128,880 A | 12/1978 | Cray, Jr. | |
| 4,221,997 A | 9/1980 | Flemming | |
| 4,367,998 A | 1/1983 | Causer | |
| 4,401,852 A | 8/1983 | Noso et al. | |
| 4,456,961 A | 6/1984 | Price et al. | |
| 4,460,302 A | 7/1984 | Moreau et al. | |
| 4,474,174 A | 10/1984 | Petruzzi | |
| 4,491,135 A | 1/1985 | Klein | |
| 4,503,854 A | 3/1985 | Jako | |
| 4,517,963 A | 5/1985 | Michel | |
| 4,523,884 A | 6/1985 | Clement et al. | |
| 4,586,398 A | 5/1986 | Yindra | |
| 4,604,016 A | 8/1986 | Joyce | |
| 4,616,637 A | 10/1986 | Caspari et al. | |
| 4,624,011 A | 11/1986 | Watanabe et al. | |
| 4,633,389 A | 12/1986 | Tanaka et al. | |
| 4,635,292 A | 1/1987 | Mori et al. | |
| 4,635,479 A | 1/1987 | Salisbury, Jr. et al. | |
| 4,641,292 A | 2/1987 | Tunnell et al. | |
| 4,655,257 A | 4/1987 | Iwashita | |
| 4,672,963 A | 6/1987 | Barken | |
| 4,676,243 A | 6/1987 | Clayman | |
| 4,728,974 A | 3/1988 | Nio et al. | |
| 4,762,455 A | 8/1988 | Coughlan et al. | |
| 4,791,934 A | 12/1988 | Brunnett | |
| 4,791,940 A | 12/1988 | Hirschfeld et al. | |
| 4,794,912 A | 1/1989 | Lia | |
| 4,815,006 A | 3/1989 | Andersson et al. | |
| 4,815,450 A | 3/1989 | Patel | |
| 4,837,734 A | 6/1989 | Ichikawa et al. | |
| 4,852,083 A | 7/1989 | Niehaus et al. | |
| 4,853,874 A | 8/1989 | Iwamoto et al. | |
| 4,854,301 A | 8/1989 | Nakajima | |
| 4,860,215 A | 8/1989 | Seraji | |
| 4,863,133 A | 9/1989 | Bonnell | |
| 4,883,400 A | 11/1989 | Kuban et al. | |
| 4,930,494 A | 6/1990 | Takehana et al. | |
| 4,945,479 A | 7/1990 | Rusterholz et al. | |
| 4,949,717 A | 8/1990 | Shaw | |
| 4,954,952 A | 9/1990 | Ubhayakar et al. | |
| 4,965,417 A | 10/1990 | Massie | |
| 4,969,709 A | 11/1990 | Sogawa et al. | |
| 4,969,890 A | 11/1990 | Sugita et al. | |
| 4,979,933 A | 12/1990 | Runge | |
| 4,979,949 A | 12/1990 | Matsen, III et al. | |
| 4,980,626 A | 12/1990 | Hess et al. | |
| 4,989,253 A | 1/1991 | Liang et al. | |
| 4,996,975 A | 3/1991 | Nakamura | |
| 5,019,968 A | 5/1991 | Wang et al. | |
| 5,020,001 A | 5/1991 | Yamamoto et al. | |
| 5,046,375 A | 9/1991 | Salisbury, Jr. et al. | |
| 5,065,741 A | 11/1991 | Uchiyama et al. | |
| 5,078,140 A | 1/1992 | Kwoh | |
| 5,086,401 A | 2/1992 | Glassman et al. | |
| 5,091,656 A | 2/1992 | Gahn | |
| 5,097,829 A | 3/1992 | Quisenberry | |
| 5,097,839 A | 3/1992 | Allen | |
| 5,098,426 A | 3/1992 | Sklar et al. | |
| 5,105,367 A | 4/1992 | Tsuchihashi et al. | |
| 5,109,499 A | 4/1992 | Inagami et al. | |
| 5,123,095 A | 6/1992 | Papadopulos et al. | |
| 5,131,105 A | 7/1992 | Harrawood et al. | |
| 5,142,930 A | 9/1992 | Allen et al. | |
| 5,145,227 A | 9/1992 | Monford, Jr. | |
| 5,166,513 A | 11/1992 | Keenan et al. | |
| 5,175,694 A | 12/1992 | Amato | |
| 5,182,641 A | 1/1993 | Diner et al. | |
| 5,184,601 A | 2/1993 | Putman | |
| 5,187,574 A | 2/1993 | Kosemura et al. | |
| 5,196,688 A | 3/1993 | Hesse et al. | |
| 5,201,325 A | 4/1993 | McEwen et al. | |
| 5,201,743 A | 4/1993 | Haber et al. | |
| 5,217,003 A | 6/1993 | Wilk | |
| 5,221,283 A | 6/1993 | Chang | |
| 5,228,429 A | 7/1993 | Hatano | |
| 5,230,623 A | 7/1993 | Guthrie et al. | |
| 5,236,432 A | 8/1993 | Matsen, III et al. | |
| 5,251,127 A | 10/1993 | Raab | |
| 5,257,999 A | 11/1993 | Slanetz, Jr. | |
| 5,271,384 A | 12/1993 | McEwen et al. | |
| 5,279,309 A | 1/1994 | Taylor et al. | |
| 5,282,806 A | 2/1994 | Haber | |
| 5,289,273 A | 2/1994 | Lang | |
| 5,289,365 A | 2/1994 | Caldwell et al. | |
| 5,299,288 A | 3/1994 | Glassman et al. | |
| 5,300,926 A | 4/1994 | Stoeckl | |
| 5,303,148 A | 4/1994 | Mattson et al. | |
| 5,304,185 A | 4/1994 | Taylor | |
| 5,305,203 A | 4/1994 | Raab | |
| 5,305,427 A | 4/1994 | Nagata | |
| 5,309,717 A | 5/1994 | Minch | |
| 5,313,306 A | 5/1994 | Kuban et al. | |
| 5,320,630 A | 6/1994 | Ahmed | |
| 5,337,732 A | 8/1994 | Grundfest et al. | |
| 5,339,799 A | 8/1994 | Kami et al. | |
| 5,343,385 A | 8/1994 | Joskowicz et al. | |
| 5,343,391 A | 8/1994 | Mushabac | |
| 5,345,538 A | 9/1994 | Narayannan et al. | |
| 5,357,962 A | 10/1994 | Green | |
| 5,368,015 A | 11/1994 | Wilk | |
| 5,368,428 A | 11/1994 | Hussey et al. | |
| 5,371,536 A | 12/1994 | Yamaguchi | |
| 5,382,885 A | 1/1995 | Salcudean et al. | |
| 5,388,987 A | 2/1995 | Badoz et al. | |
| 5,395,369 A | 3/1995 | McBrayer et al. | |
| 5,397,323 A | 3/1995 | Taylor et al. | |
| 5,402,801 A | 4/1995 | Taylor | |
| 5,403,319 A | 4/1995 | Matsen, III et al. | |
| 5,408,409 A | 4/1995 | Glassman et al. | |
| 5,410,638 A | 4/1995 | Colgate et al. | |
| 5,417,210 A | 5/1995 | Funda et al. | |
| 5,417,701 A | 5/1995 | Holmes | |
| 5,422,521 A | 6/1995 | Neer et al. | |
| 5,431,645 A | 7/1995 | Smith et al. | |
| 5,434,457 A | 7/1995 | Josephs et al. | |
| 5,442,728 A | 8/1995 | Kaufman et al. | |
| 5,443,484 A | 8/1995 | Kirsch et al. | |
| 5,445,166 A | 8/1995 | Taylor | |
| 5,451,924 A | 9/1995 | Massimino et al. | |
| 5,455,766 A | 10/1995 | Schaller et al. | |
| 5,458,547 A | 10/1995 | Teraoka et al. | |
| 5,458,574 A | 10/1995 | Machold et al. | |
| 5,476,010 A | 12/1995 | Fleming et al. | |
| 5,490,117 A | 2/1996 | Oda et al. | |
| 5,490,843 A | 2/1996 | Hildwein et al. | |
| 5,506,912 A | 4/1996 | Nagasaki et al. | |
| 5,512,919 A | 4/1996 | Araki | |
| 5,515,478 A | 5/1996 | Wang | |
| 5,544,654 A | 8/1996 | Murphy et al. | |
| 5,553,198 A | 9/1996 | Wang et al. | |
| 5,562,503 A | 10/1996 | Ellman et al. | |
| 5,571,110 A | 11/1996 | Matsen, III et al. | |
| 5,572,999 A | 11/1996 | Funda et al. | |
| 5,609,560 A | 3/1997 | Ichikawa et al. | |
| 5,626,595 A | 5/1997 | Sklar et al. | |
| 5,629,594 A | 5/1997 | Jacobus et al. | |
| 5,630,431 A | 5/1997 | Taylor | |
| 5,631,973 A | 5/1997 | Green | |
| 5,636,259 A | 6/1997 | Khutoryansky et al. | |
| 5,649,956 A | 7/1997 | Jensen et al. | |
| 5,657,429 A | 8/1997 | Wang et al. | |
| 5,658,250 A | 8/1997 | Blomquist et al. | |
| 5,676,673 A | 10/1997 | Ferre et al. | |

| | | |
|---|---|---|
| 5,695,500 A | 12/1997 | Taylor et al. |
| 5,696,574 A | 12/1997 | Schwaegerle |
| 5,696,837 A | 12/1997 | Green |
| 5,718,038 A | 2/1998 | Takiar et al. |
| 5,727,569 A | 3/1998 | Benetti et al. |
| 5,735,290 A | 4/1998 | Sterman et al. |
| 5,737,711 A | 4/1998 | Abe |
| 5,749,362 A | 5/1998 | Funda et al. |
| 5,754,741 A | 5/1998 | Wang et al. |
| 5,762,458 A | 6/1998 | Wang et al. |
| 5,766,126 A | 6/1998 | Anderson |
| 5,776,126 A | 7/1998 | Wilk et al. |
| 5,779,623 A | 7/1998 | Bonnell |
| 5,792,135 A | 8/1998 | Madhani et al. |
| 5,792,178 A | 8/1998 | Welch et al. |
| 5,797,900 A | 8/1998 | Madhani et al. |
| 5,800,423 A | 9/1998 | Jensen |
| 5,807,284 A | 9/1998 | Foxlin |
| 5,807,377 A | 9/1998 | Madhani et al. |
| 5,807,378 A | 9/1998 | Jensen et al. |
| 5,808,665 A | 9/1998 | Green |
| 5,810,880 A | 9/1998 | Jensen et al. |
| 5,813,813 A | 9/1998 | Daum et al. |
| 5,814,038 A | 9/1998 | Jensen et al. |
| 5,817,084 A | 10/1998 | Jensen |
| 5,825,982 A | 10/1998 | Wright et al. |
| 5,827,319 A | 10/1998 | Carlson et al. |
| 5,836,869 A | 11/1998 | Kudo et al. |
| 5,844,824 A | 12/1998 | Newman et al. |
| 5,855,553 A * | 1/1999 | Tajima et al. ............... 600/407 |
| 5,855,583 A | 1/1999 | Wang et al. |
| 5,859,934 A | 1/1999 | Green |
| 5,860,995 A | 1/1999 | Berkelaar |
| 5,876,325 A | 3/1999 | Mizuno et al. |
| 5,878,193 A | 3/1999 | Wang et al. |
| 5,882,206 A | 3/1999 | Gillio |
| 5,887,121 A | 3/1999 | Funda et al. |
| 5,898,599 A | 4/1999 | Massie et al. |
| 5,904,702 A | 5/1999 | Ek et al. |
| 5,906,630 A | 5/1999 | Anderhub et al. |
| 5,911,036 A | 6/1999 | Wright et al. |
| 5,920,395 A | 7/1999 | Schultz |
| 5,931,832 A | 8/1999 | Jensen |
| 5,950,629 A | 9/1999 | Taylor et al. |
| 5,951,475 A | 9/1999 | Gueziec et al. |
| 5,951,587 A | 9/1999 | Qureshi et al. |
| 5,954,731 A | 9/1999 | Yoon |
| 5,957,902 A | 9/1999 | Teves |
| 5,980,782 A | 11/1999 | Hershkowitz et al. |
| 5,984,932 A | 11/1999 | Yoon |
| 6,024,695 A | 2/2000 | Taylor et al. |
| 6,080,181 A | 6/2000 | Jensen et al. |
| 6,106,511 A | 8/2000 | Jensen |
| 6,120,433 A | 9/2000 | Mizuno et al. |
| 6,132,368 A | 10/2000 | Cooper |
| 6,201,984 B1 | 3/2001 | Funda et al. |
| 6,206,903 B1 | 3/2001 | Ramans |
| 6,223,100 B1 | 4/2001 | Green |
| 6,226,566 B1 | 5/2001 | Funda et al. |
| 6,231,526 B1 | 5/2001 | Taylor et al. |
| 6,246,200 B1 | 6/2001 | Blumenkranz et al. |
| 6,259,806 B1 | 7/2001 | Green et al. |
| 6,292,712 B1 | 9/2001 | Bullen |
| 6,309,397 B1 | 10/2001 | Julian et al. |
| 6,312,435 B1 | 11/2001 | Wallace et al. |
| 6,331,181 B1 | 12/2001 | Tierney et al. |
| 6,346,072 B1 | 2/2002 | Cooper |
| 6,364,888 B1 | 4/2002 | Niemeyer et al. |
| 6,371,952 B1 | 4/2002 | Madhani et al. |
| 6,402,737 B1 | 6/2002 | Tajima et al. |
| 6,470,236 B2 * | 10/2002 | Ohtsuki ............... 700/247 |
| 6,490,490 B1 | 12/2002 | Uchikubo et al. |
| 6,522,906 B1 | 2/2003 | Salisbury, Jr. et al. |
| 6,659,939 B2 | 12/2003 | Moll et al. |
| 6,837,883 B2 * | 1/2005 | Moll et al. ............... 606/1 |

FOREIGN PATENT DOCUMENTS

| | | |
|---|---|---|
| DE | 4310842 | 1/1995 |
| EP | 239409 | 9/1987 |
| EP | 424687 | 5/1991 |
| EP | 776738 | 6/1997 |
| WO | WO-9104711 | 4/1991 |
| WO | WO-9220295 | 11/1992 |
| WO | WO-9313916 | 7/1993 |
| WO | WO-9418881 | 9/1994 |
| WO | WO-9426167 | 11/1994 |
| WO | WO-97-15240 | 5/1997 |
| WO | WO-9825666 | 6/1998 |

OTHER PUBLICATIONS

Abstract of a presentation "3-D Vision Technology Applied to Advanced Minimally Invasive Surgery Systems" given at the 3rd World Congress of Endoscopic Surgery in Bordeaux, (Jun. 18-20, 1992), entitled "Session 15/3" (1 page total).

Abstract of a presentation "A Pneumatic Controlled Sewing Device for Endoscopic Application the MIS Sewing Instrument MSI" given at the 3rd World Congress of Endoscopic Surgery in Bordeaux, Jun. 18-20, 1992 (1 page total).

Abstract of a presentation "Concept and Experimental Application of a Surgical Robotic System the Steerable MIS Instrument SMI" given at the 3rd World Congress of Endoscopic Surgery in Bordeaux, Jun. 18-20, 1992 (1 page total).

Abstract of a presentation given at the 3rd World Congress of Endoscopic Surgery in Bordeaux (Jun. 18-20, 1992), entitled "Session 15/2" (1 page total).

Abstract of a presentation given at the 3rd World Congress of Endoscopic Surgery in Bordeaux (Jun. 18-20, 1992), entitled "Session 15/4" (1 page total).

Abstract of a presentation given at the 3rd World Congress of Endoscopic Surgery in Bordeaux (Jun. 18-20, 1992), entitled "Session 15/5" (1 page total).

Abstract of a presentation given at the 3rd World Congress of Endoscopic Surgery in Bordeaux, (Jun. 18-20, 1992), entitled "Session 15/1" (1 page total).

Alexander, III, "A Survey Study of Teleoperators, Robotics, and Remote Systems Technology," Remotely Manned Systems—Exploration and Operation in Space, California Institute of Technology 1973, pp. 449-458.

Alexander, III, "Impacts of Telemation on Modern Society," On the Theory and Practice of Robots and Manipulators vol. II, 1974, pp. 121-136.

Bejczy, "Controlling Remote Manipulators through Kinesthetic Coupling," Computers in Mechanical Engineering 1983, pp. 48-60.

Besant et al., Abstract of a presentation "Camera Control for Laparoscopic Surgery by Speech-Recognizing Robot: Constant Attention and Better Use of Personnel," given at the 3rd World Congress of Endoscopic Surgery in Bordeaux, Jun. 18-20, 1992 (1 page total).

Charles et al., "Design of a Surgeon-Machine Interface for Teleoperated Microsurgery," IEEE 1989 (3 pages total).

Colgate, "Power and Impedance Scaling in Bilateral Manipulation," IEEE 1991, pp. 2292-2297.

Corcoran, "Robots for the Operating Room," The New York Times, Sunday Jul. 19, 1992, Section 3, p. 9, col. 1 (2 pages total).

Das et al., "Kinematic Control and Visual Display of Redundant Teleoperators," IEEE 1989 pp. 1072-1077.

Dolan et al., "A Robot in an Operating Room: A Bull in a China Shop," IEEE, 1987, pp. 1096-1097.

Gayed et al., "An Advanced Control Micromanipulator for Surgical Applications," Systems Science vol. 13, 1987, pp. 23-34.

Green et al., Abstract of a presentation "Telepresence: Advanced Teleoperator Technology for Minimally Invasive Surgery," given at "Medicine meets virtual reality" symposium in San Diego, Jun. 4-7, 1992 (20 pages total).

Green et al., Abstract of a presentation "Telepresence: Advanced Teleoperator Technology for Minimally Invasive Surgery," given at the 3rd World Congress of Endoscopic Surgery in Bordeaux, Jun. 18-20, 1992 (2 pages total).

Green, Statutory Declaration of Dr. Philip S. Green, presenter of the video entitled "Telepresence Surgery—The Future of Minimally Invasive Medicine" (32 pages total).

Guerrouad et al., "S.M.O.S.: Stereotaxical Microtelemanipulator for Ocular Surgery," IEEE, 1989, pp. 879-880.

Inoue et al., "Six-axis Bilateral Control of an Articulated Slave Manipulator Using a Cartesian Master Manipulator," Advanced Robotics, 4, No. 2, 1990, pp. 139-150.

Kazerooni, "Human/Robot Interaction via the Transfer of Power and Information Signals—Part I: Dynamics and Control Analysis," IEEE, 1989, pp. 1632-1640.

Kazerooni, "Human/Robot Interaction via the Transfer of Power and Information Signals—Part II: An Experimental Analysis," IEEE, 1989, pp. 1641-1647.

Krishnan et al., Abstract of a presentation "Design Considerations of a New Generation Endoscope Using Robotics and Computer Vision Technology," given at the 3rd World Congress of Endoscopic Surgery in Bordeaux, Jun. 18-20, 1992 (1 page total).

Lavallee, "A New System for Computer Assisted Neurosurgery," IEEE, 1989, vol. 11, pp. 926-927.

Mair, Industrial Robotics, Prentice Hall, 1988, pp. 41-43, 49-50, 54, 203-209.

Majima et al., "On a Micro-Manipulator for Medical Application—Stability Consideration of its Bilateral Controller," Mechatronics, 1991, pp. 293-309.

NASA, "Anthropomorphic Remote Manipulator", NASA Tech Briefs, 1991 (1 page total).

Preising et al., "A Literature Review: Robots in Medicine," IEEE, Jun. 1991, pp. 13-22 & 71.

Rasor et al., "Endocorporeal Surgery Using Remote Manipulators," Remotely Manned Systems—Exploration and Operation in Space, California Institute of Technology 1973, pp. 483-492.

Sabatini et al., "Force Feedback-Based Telemicromanipulation for Robot Surgery on Soft Tissues," IEEE, 1989, pp. 890-891.

Taubes, "Surgery in Cyberspace," Discover Magazine, Dec. 1994, pp. 85-92.

Taylor et al., "Taming the Bull: Safety in a Precise Surgical Robot," IEEE, 1991, pp. 865-871.

Tejima, "A New Microsurgical Robot System for Corneal Transplantation," Precision Machinery, 1988 vol. 2, pp. 1-9.

Tendick et al., "Analysis of the Surgeon's Grasp for Telerobotic Surgical Manipulation," IEEE, 1989, pp. 914-915.

Thring, "Robots and Telechirs: Manipulator with Memory: Remote Manipulators: Machine Limbs for the Handicapped," Wiley & Sons, 1983 (26 pages total).

Transcript of a video presented by SRI at the 3rd World Congress of Endoscopic Surgery in Bordeaux on Jun. 18-20, 1992, in Washington on Apr. 9, 1992, and in San Diego, CA, on Jun. 4-7, 1992 entitled "Telepresence Surgery—The Future of Minimally Invasive Medicine" (3 pages total).

Trevelyan et al., "Motion Control for a Sheep Shearing Robot," Proceedings of the 1st International Symposium on Robotics Research, MIT, Cambridge, Massachusetts, USA, 1983, pp. 175-190.

Vibet, "Properties of Master-Slave Robots," Motor-con, 1987, pp. 309-314.

Wolf et al., "Student Reference Manual for Electronic Instrumentation Laboratories," Prentice Hall, New Jersey 1990, pp. 498-499.

* cited by examiner

MINIMALLY INVASIVE SURGICAL TRAINING USING ROBOTICS AND TELECOLLABORATION

CROSS-REFERENCES TO RELATED APPLICATIONS

The present application is a divisional of U.S. application Ser. No. 10/246,236, filed Sep. 17, 2002, now U.S. Pat. No. 6,951,535, the full disclosure of which is incorporated herein by reference.

BACKGROUND OF THE INVENTION

The present invention relates to a medical robotic system.

Historically, surgery has been performed by making large incisions in a patient to provide access to the surgical site. There has been developed instruments that allow a surgeon to perform a procedure through small incisions in the patient. The instruments include an endoscope which has a camera that allows the surgeon to view the internal organs of the patient through a small incision. Such procedures are less traumatic to the patient and have shorter recovery times than conventional surgical procedures.

Such instruments have even been used to perform minimally invasive heart surgery. Blockage of a coronary artery may deprive the heart of blood and oxygen required to sustain life. The blockage may be removed with medication or by an angioplasty. For severe blockage "a coronary artery bypass graft (CABG) is performed to bypass the blocked area of the artery. CABG procedures are typically performed by splitting the sternum and pulling open the chest cavity to provide access to the heart. An incision is made in the artery adjacent to the blocked area. The internal mammary artery is then severed and attached to the artery at the point of incision. The internal mammary artery bypasses the blocked area of the artery to again provide a full flow of blood to the heart. Splitting the sternum and opening the chest cavity can create a tremendous trauma to the patient. Additionally, the cracked sternum prolongs the recovery period of the patient.

Computer Motion of Goleta, Calif. provides a system under the trademark ZEUS that allows a surgeon to perform minimally invasive surgery, including CAGB procedures. The procedure is performed with instruments that are inserted through small incisions in the patient's chest. The instruments are controlled by robotic arms. Movement of the robotic arms and actuation of instrument end effectors are controlled by the surgeon through a pair of handles and a foot pedal that are coupled to an electronic controller. Alternatively, the surgeon can control the movement of an endoscope used to view the internal organs of the patient through voice commands.

The handles and a screen are typically integrated into a console that is operated by the surgeon to control the various robotic arms and medical instruments of a ZEUS system. Utilizing a robotic system to perform surgery requires a certain amount of training. It would be desirable to provide a system that would allow a second surgeon to assist another surgeon in controlling a robotic medical system. The second surgeon could both teach and assist a surgeon learning to perform a medical procedure with a ZEUS system. This would greatly reduce the time required to learn the operation of a robotically assisted medical system.

U.S. Pat. No. 5,217,003 issued to Wilk discloses a surgical system which allows a surgeon to remotely operate robotically controlled medical instruments through a telecommunication link. The Wilk system only allows for one surgeon to operate the robotic arms at a given time. Wilk does not disclose or contemplate a system which allows two different surgeons to operate the same set of robotic arms.

U.S. Pat. No. 5,609,560 issued to Ichikawa et al. and assigned to Olympus Optical Co. Ltd. discloses a system that allows an operator to control a plurality of different medical devices through a single interface. The Olympus patent does not disclose a system which allows multiple surgeons to simultaneously perform a surgical procedure.

BRIEF SUMMARY OF THE INVENTION

A medical system that includes a first input device that can move a first input distance to move a first medical device and a second input device that can move a second input distance to move said first medical device. The system may further have a feedback device that can provide an indication of a difference between the first and second input distances.

DETAILED DESCRIPTION OF THE INVENTION

Figure 1:
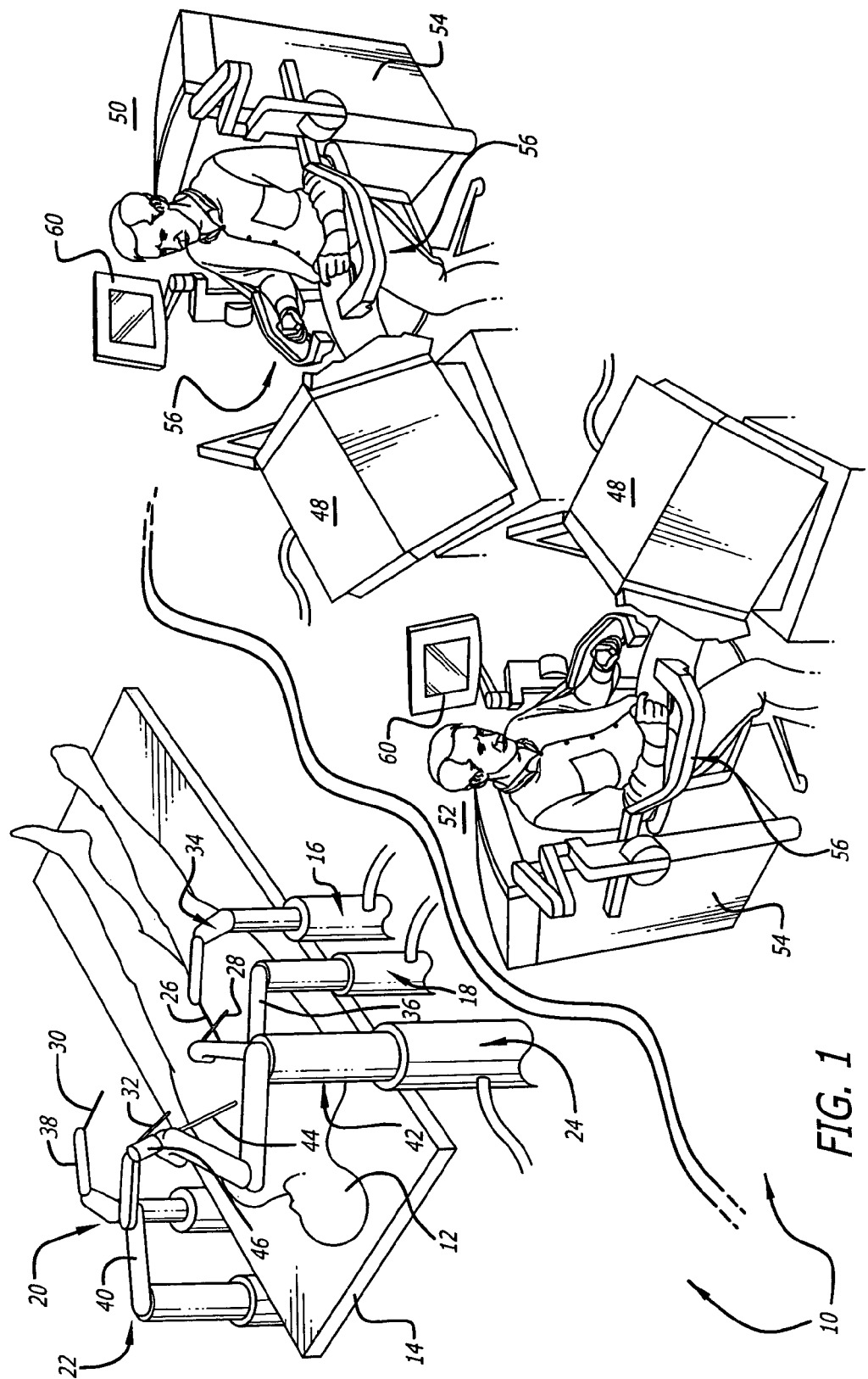
FIG. 1 is a perspective view of a medical robotic system.

Referring to the drawings more particularly by reference numbers, FIG. 1 shows a system 10 that can perform minimally invasive surgery. In one embodiment, the system 10 is used to perform a minimally invasive coronary artery bypass graft (MI-CABG) and other anastomostic procedures. Although a MI-CABG procedure is shown and described, it is to be understood that the system may be used for other surgical procedures. For example, the system can be used to suture any pair of vessels. The system 10 can be used to perform a procedure on a patient 12 that is typically lying on an operating table 14. Mounted to the operating table 14 is a first articulate arm 16, a second articulate arm 18, a third articulate arm 20, a fourth articulate arm 22 and a fifth articulate arm 24 which may also be referred to as medical devices. The articulate arms 16, 18, 20, 22 and 24 are preferably mounted to the table 14 so that the arms are at a same reference plane as the patient. Although five articulate arms are shown and described, it is to be understood that the system may have any number of arms.

The first 16, second 18, third 20 and fourth 22 articulate arms may each have a surgical instrument 26, 28, 30 and 32, respectively, coupled to robotic arms 34, 36, 38 and 40, respectively. The fifth articulate arm 24 includes a robotic arm 42 that holds and moves an endoscope 44. The instruments 26, 28, 30 and 32, and endoscope 44 are inserted through incisions cut into the skin of the patient 12. The endoscope 44 has a camera 46 that is coupled to video consoles 48 which display images of the internal organs of the patient.

The system 10 may include a mentor control unit (MCU) 50 and a pupil control unit (PCU) 52. Each control unit 50 and 52 has a controller 54 and a pair of handle assemblies 56 that allow a mentor surgeon at the MCU 50 to teach and assist a pupil surgeon at the PCU 52. The PCU 52 is typically in the operating room. The MCU 50 may be at a remote location. Each controller, 54 contains electrical circuits, such as a processor(s), memory, I/O interface, drivers, etc. that control the movement and actuation of robotic arms 34, 36, 38, 40 and 42 and instruments 26, 28, 30 and 32. The surgeon can view a different portion of the patient by providing a voice command(s) that moves the arm 42 holding the endoscope 44. The robotic arm(s) maybe devices that are sold by the assignee of the present invention, Computer Motion, Inc. of Goleta, Calif., under the trademark AESOP. The system is also described in U.S. Pat. No. 5,657,429 issued to Wang et al. and assigned to Computer Motion, which is hereby incorporated by reference.

Any two instruments 26, 28, 30 or 32 can be controlled by the handle assemblies 56 of each control unit 50 and 52. For example, instruments 26 and 28 can be controlled by the handle assemblies 56 of the MCU 50 and instruments 30 and 32 can be controlled by the handle assemblies of the PCU 52. Alternatively, a single instrument may be controlled by handle assemblies 56 of both the MCU 50 and PCU 52.

The handle assemblies 56 and articulate arms 16, 18, 20 and 22 have a master-slave relationship so that movement of the handles 56 produces a corresponding movement of the surgical instruments 26, 28, 30 and/or 32. The controller 54 receives input signals from the handle assemblies 56 of each control unit 50 and 52, computes a corresponding movement of the surgical instruments 26, 28, 30 and 32, and provides output signals to move the robotic arms 34, 36, 38 and 40 and instruments 26, 28, 30 and 32. The entire system may be similar to a product marketed by Computer Motion under the trademark ZEUS. The operation of the system is also described in U.S. Pat. No. 5,762,458 issued to Wang et al. and assigned to Computer Motion, which is hereby incorporated by reference.

Figure 2:
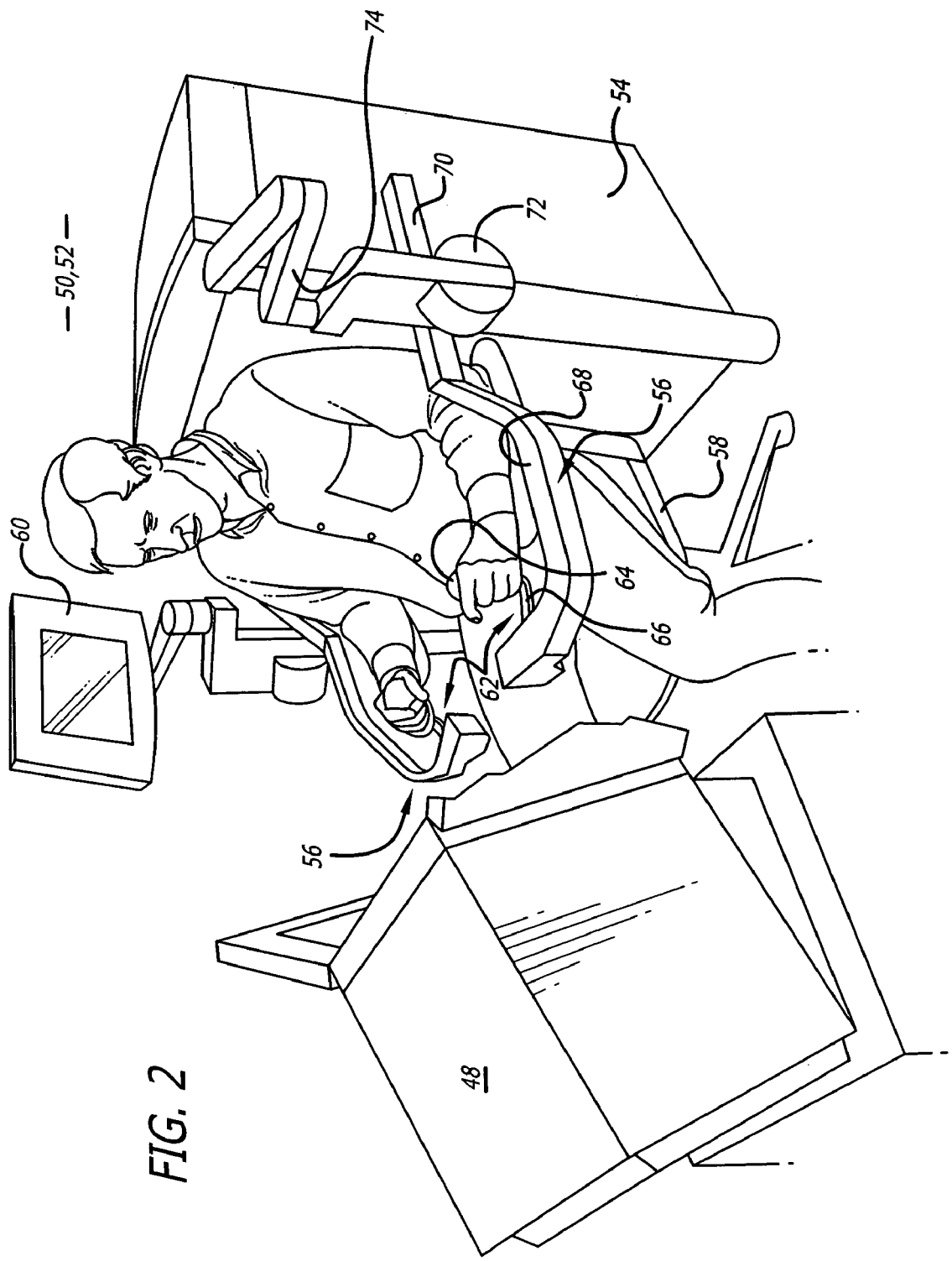
FIG. 2 is a perspective view of a control unit.

FIG. 2 shows a control unit 50 or 52. The handle assemblies 56 are located adjacent to a surgeon's chair 58. The handle assemblies 56 are coupled to the controller 54. The controller 54 is coupled to the robotic arms 34, 36, 38, 40 and 42 and medical instruments 26, 28, 30 and 32. The controller 54 may include one or more microprocessors, memory devices, drivers, etc. that convert input information from the handle assemblies 56 into output control signals which move the robotic arms 34, 36, 38 and 40 and/or actuate the medical instruments 26, 28, 30 and 32.

The surgeon's chair 58 and handle assemblies 56 may be in front of the video console 48. The video console 48 may be linked to the endoscope 44 shown in FIG. 1 to provide video images of the patient. The control unit 50 or 52 may also include a computer screen 60 coupled to the controller 54. The screen 60 may display graphical user interfaces (GUIs) that allow the surgeon to control various functions and parameters of the system 10. The control unit 50 or 52 may further have a microphone (not shown) to accept voice commands. One or more voice commands may be used to move the endoscope. Other voice commands can be used to vary parameters of the system. The voice control and parameter changing system may be the same or similar to a product sold by Computer Motion under the trademark HERMES.

Each handle assembly 56 may include a handle/wrist assembly 62. The handle/wrist assembly 62 has a handle 64 that is coupled to a wrist 66. The wrist 66 is connected to a forearm linkage 68 that slides along a slide bar 70. The slide bar 70 is pivotally connected to an elbow joint 72. The elbow joint 72 is pivotally connected to a shoulder joint 74 that is attached to the controller 54.

Figure 3:
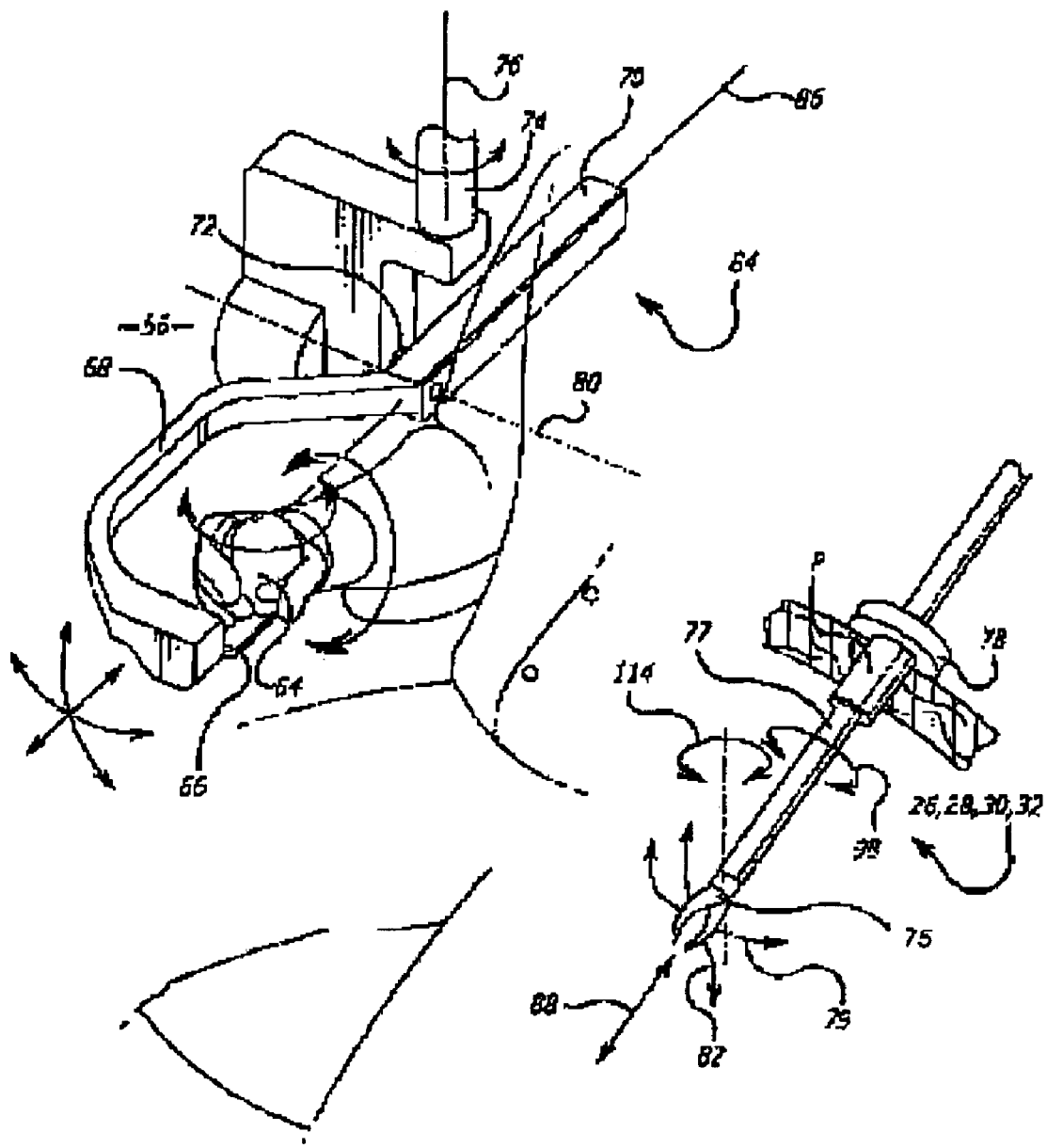
FIG. 3 is a perspective view of a handle assembly of the control unit.

FIG. 3 shows a handle assembly 56 superimposed with a medical instrument 26, 28, 30 or 32. The instrument 26, 28, 30 or 32 may include an end effector 75 attached to an instrument shaft 77. The shaft 77 extends through a cannula 78 inserted through an incision of a patient 12. The incision defines a pivot point P for the medical instrument 26, 28, 30 or 32.

The shoulder joint 74 includes a sensor (not shown) that provides feedback on the movement of the handle 64 about a shoulder axis 76. The sensor may be a mechanical encoder, optical encoder, etc. or other device which provides an output signal that corresponds to a position of the handle 64 about the shoulder axis 76. The output of the shoulder sensor is provided to the controller 54. The controller 54 performs a series of computations to determine a corresponding movement of the medical instrument 26, 28, 30 or 32. The computations may include one or more transformation and kinematic equations. The controller 54 provides output signals to the corresponding robotic arm to move the instrument 26, 28, 30 or 32 as indicated by the arrow 79. The transformation and kinematic equations may be similar to the equations used in the AESOP and ZEUS products with the signs (+/−) reversed to account for the shoulder axis 76 being behind the surgeon.

The shoulder joint 74 may have a force actuator (not shown) that can provide a resistive force to movement of the handle 64 about the axis 76. The force actuator maybe an active device or a passive device such as a friction clutch.

The elbow joint 72 includes a sensor (not shown) that provides positional feedback on the position of the assembly about an elbow axis 80. The controller 54 utilizes the positional feedback to drive the robotic arm and move the instrument in the direction indicated by the arrow 82.

The elbow joint 72 may also have a force actuator (not shown) that can provide resistance to movement of the handle about the axis 80. When transforming movement of the handle 64 to movement of the instrument 26, 28, 30 or 32 the controller 54 may equate the elbow axis 80 to the instrument pivot point P. Equating the elbow axis 80 with the pivot point P provides a kinematic relationship such that the surgeon "feels" like they are actually moving the instrument. Additionally, the length of the forearm linkage and location of the handle are such that the surgeon is provided with the sensation that they are holding and moving the distal end of the instrument. These relationships also improve the ergonomics of the handle assembly and the ease of use of the robotic system as a whole.

The forearm linkage 68 and slide bar 70 create a translator 84 that allows linear movement of the linkage 68 along a translator axis 86. The translator 84 has a sensor (not shown) that provides feedback information that is used to drive the robotic arm and move the instrument 26, 28, 30 or 32 in the direction indicated by the arrows 88. The translator 84 may also have a force actuator (not shown) that can provide resistance to movement along axis 86.

Figure 4:
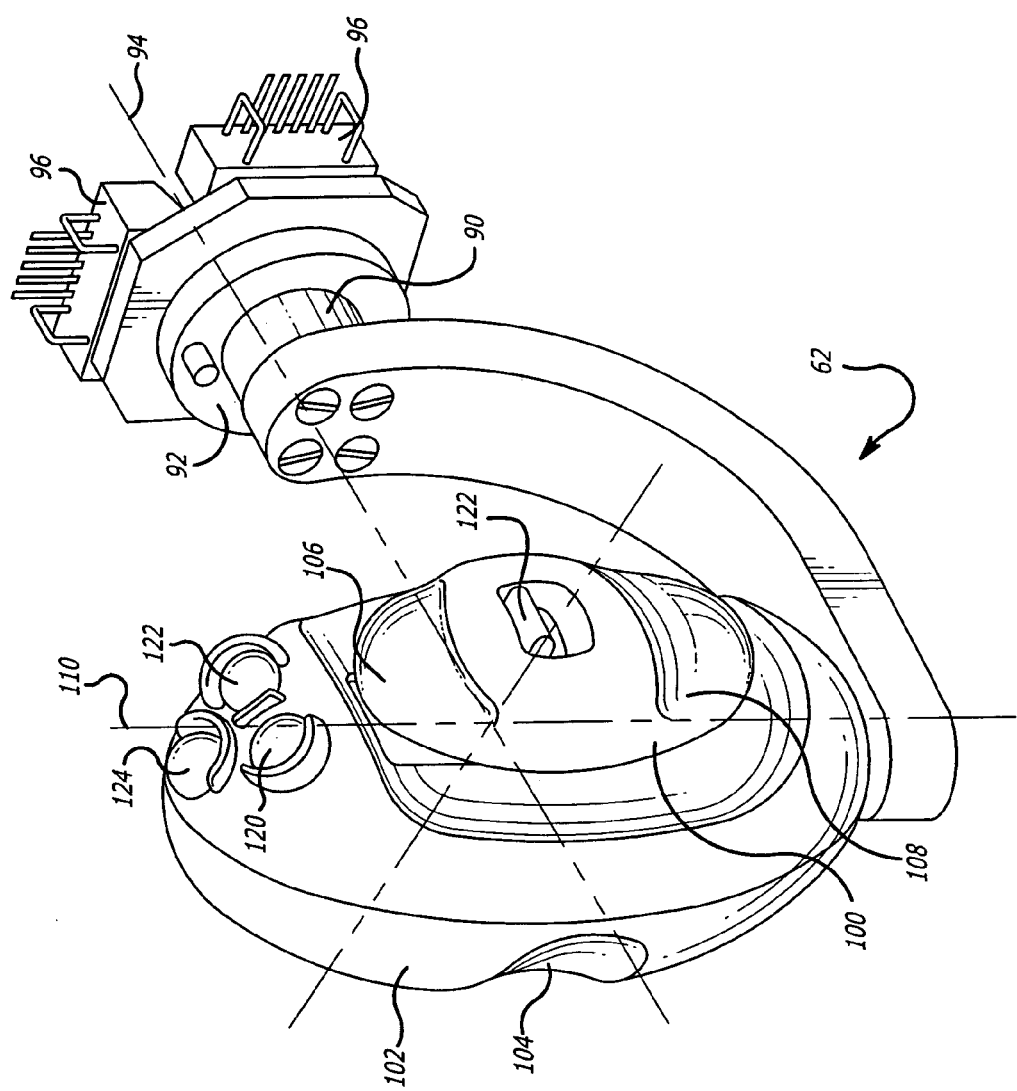
FIG. 4 is a perspective view of a handle/wrist subassembly.
Figure 5:
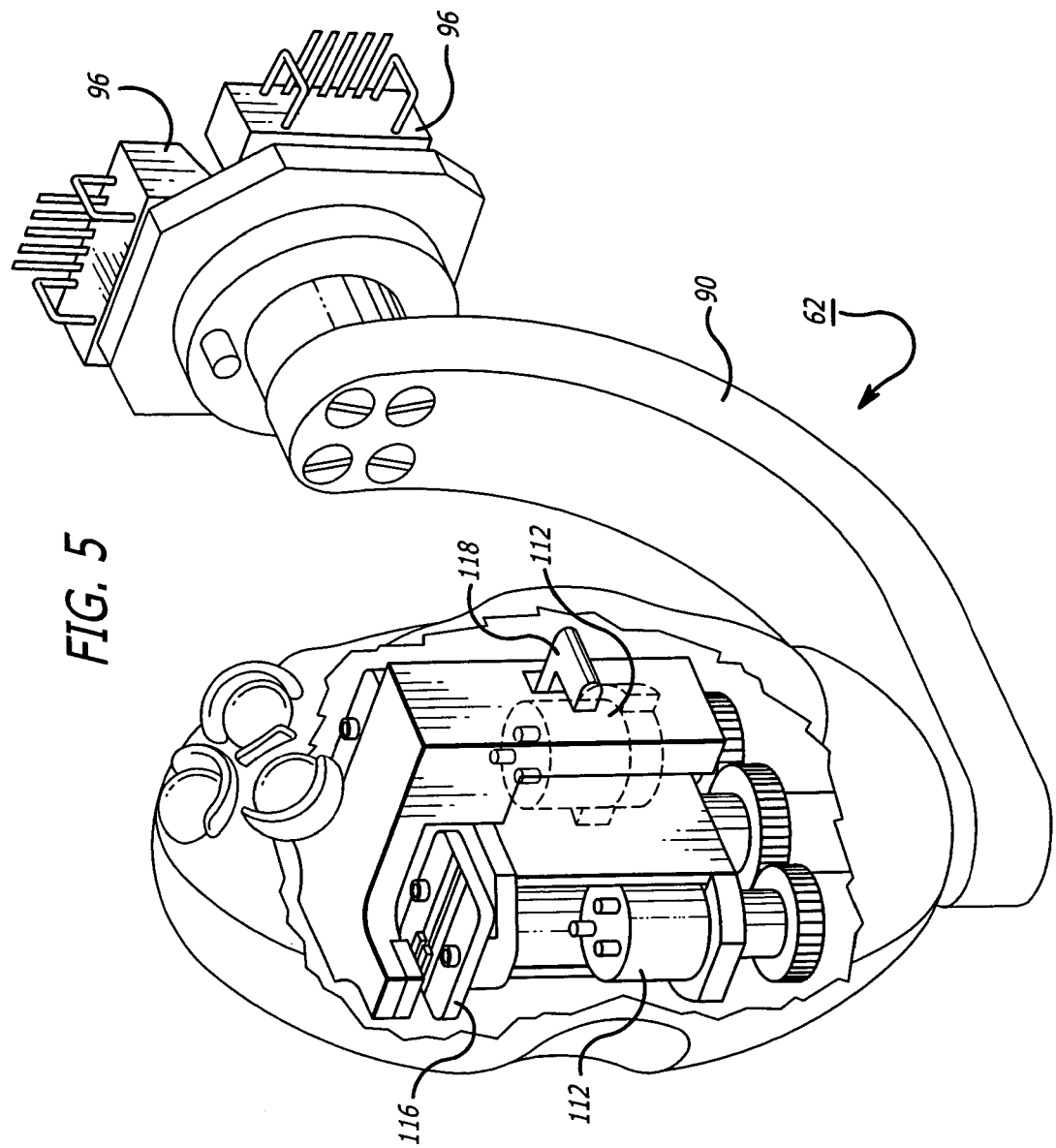
FIG. 5 is a sectional perspective view of the handle/wrist subassembly.

FIGS. 4 and 5 show the wrist/handle assembly 62. The wrist 66 includes a joint shaft 90 that is coupled to the forearm linkage (not shown) by a roll bearing 92. The roll bearing 92 allows the handle 64 to rotate about a roll axis 94. The wrist 66 may further include a sensor 96 that provides positional feedback to the controller 54. Movement of the handle 64 about the roll axis 94 may cause a corresponding rotation of the instrument end effector 75 in the direction indicated by the arrows 98 in FIG. 3. The wrist 66 may have a force actuator (not shown) that provides resistance to movement of the handle 64 about the roll axis 94.

The handle 64 includes a grasper 100 that is coupled to a handle housing 102. The housing 102 and grasper 100 are preferably shaped as an ellipsoid to allow the user to more easily grasp the handle 64 with their hand. The housing 102 may have a thumb groove 104 that receives the user's thumb. The grasper 100 may have a pair of grooves 106 and 108 to receive the index and middle fingers of the user, respectively.

The handle 64 may spin about wrist axis 110. The handle 64 may include a sensor 112 that provides positional feedback information to the controller 54 which is used to rotate the end effector 75 of the medical instrument 26, 28, 30 or 32 as indicated by the arrows 114 in FIG. 3. The handle 64 may also have a force actuator (not shown) that may provide resistance to rotation about axis.

The grasper 100 can be depressed by the user. The grasper 100 is coupled to a sensor 116 which provides feedback information to the controller 54. The feedback information is used by the controller 54 to actuate the end effector 75 shown in FIG. 3. By way of example, depressing the grasper 100 may close the end effector 75. The grasper 100 may include a switch 118 that allows the user to lock the position of the grasper 100 and the end effector 75 of the corresponding medical instrument. The locking switch 118 may be coupled to a ratchet (not shown) that allows the grasper 100 and corresponding end effector 75 to be locked at one of a number of positions. The handle 64 may also have a force actuator (not shown) that provides resistance to movement of the grasper 100.

The handle 64 have a plurality of buttons 120, 122 and 124 that can be depressed by the user. By way of example, button 120 may be used to activate a cutting mode on a cauterizing end effector. Button 122 may be used to activate a coagulating medical instrument. The button 124 may be used to vary different functions of the system.

Figure 6:
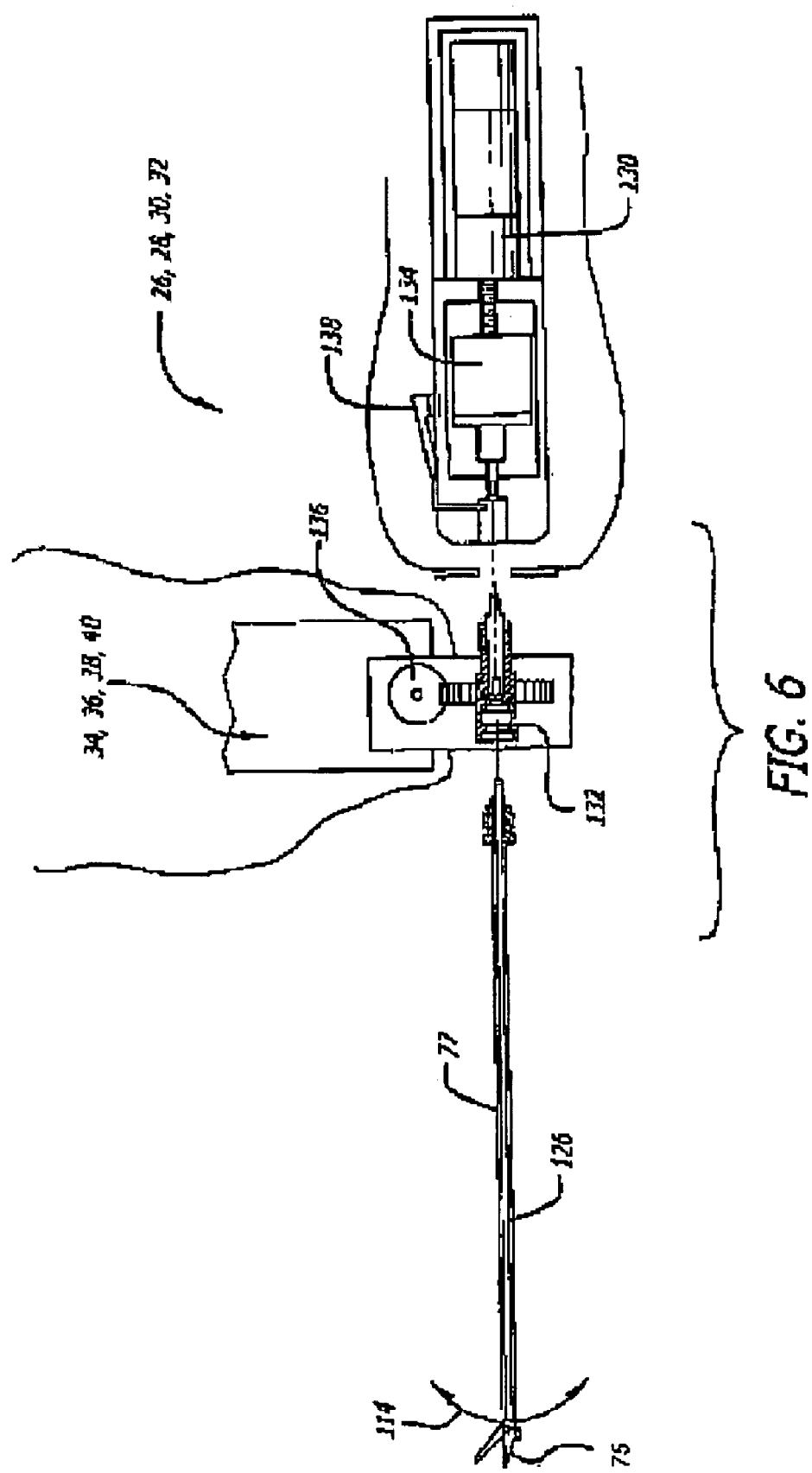
FIG. 6 is an exploded side view of an instrument of the robotic system.

FIG. 6 shows one of the surgical instruments 26, 28, 30 or 32. The instrument 26, 28, 30 or 32 may include the end effector 75 that is coupled to an actuator rod 126 located within the instrument shaft 77. The actuator rod 126 is coupled to a motor 130 by an adapter 132. The motor 130 actuates the end effector 75 by moving the actuator rod 126. The actuator rod 126 is coupled to a force sensor 134 that can sense the force being applied by the end effector 75. The force sensor 134 provides an analog output signal that is sent to a controller 54 shown in FIG. 1. Additionally, the instrument 26, 28, 30, 32 may allow movement along the arrows 114 and have a force sensor (not shown) to sense force in this direction. Each joint of the robotic arms 34, 36, 38 and 40 may also have force sensor that provide feedback to the controller 54.

The adapter 132 may be coupled to a gear assembly 136 located at the end of a robotic arm 34, 36, 38 or 40. The gear assembly 136 can rotate the adapter 132 and end effector 75. The actuator rod 126 and end effector 75 may be coupled to the force sensor 134 and motor 130 by a spring biased lever 138. The instrument 26, 28, 30 or 32 may be the same or similar to an instrument described in the '458 patent.

Figure 7:
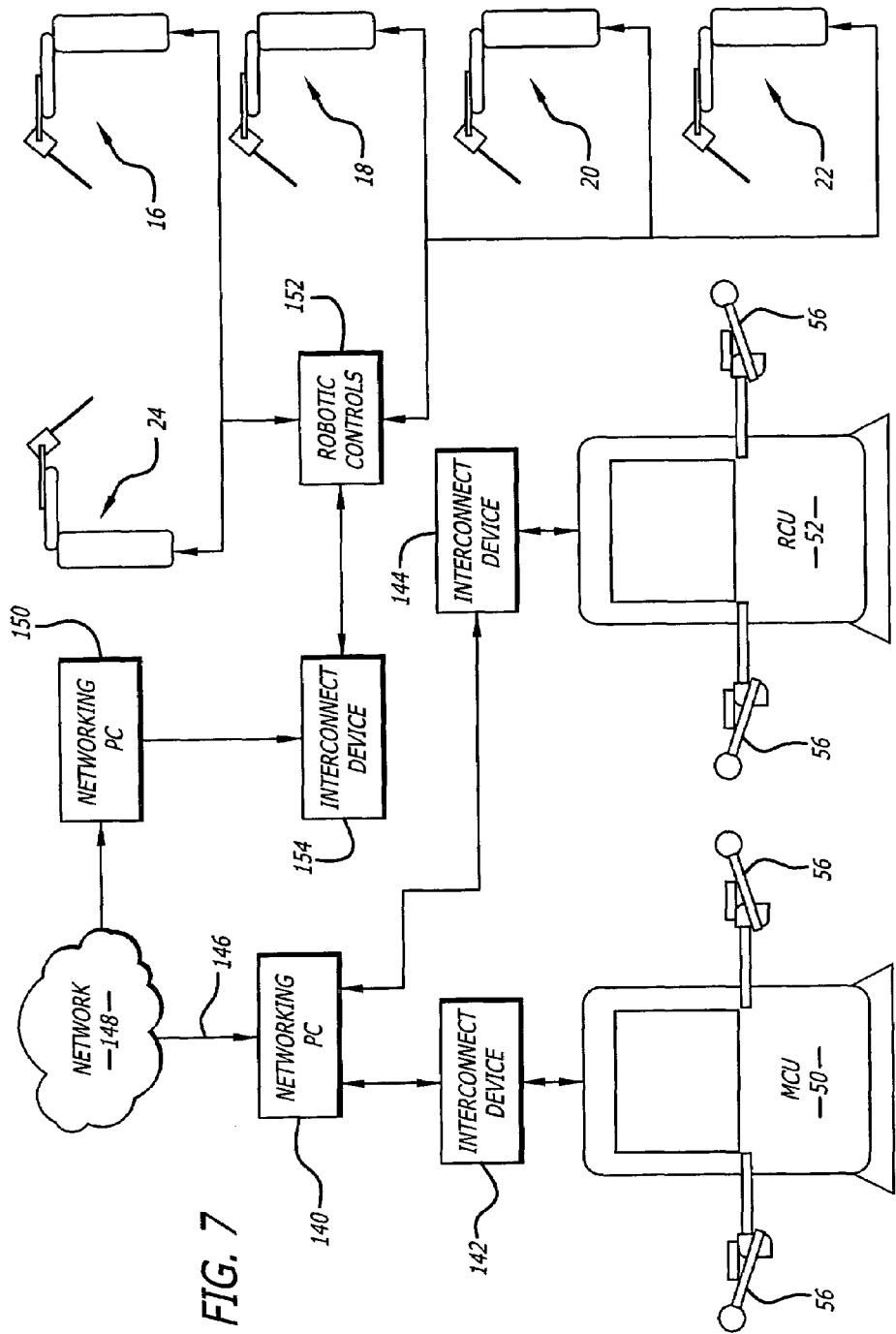
FIG. 7 is an illustration of a network system.

FIG. 7 depicts the MCU 50 and PCU 52 coupled to the articulate arms 16, 18, 20, 22 and 28 by a network port 140 and a pair of interconnect devices 142 and 144. The network port 140 may be a computer that contains the necessary hardware and software to transmit and receive information through a communication link 146 in a communication network 148.

The control units 50 and 52 may provide output signals and commands that are incompatible with a computer. The interconnect devices 142 and 144 may provide an interface that conditions the signals for transmitting and receiving signals between the control units 50 and 52 and the network computer 140.

It is to be understood that the computer 140 and/or control units 50 and 52 may be constructed so that the system does not require the interconnect devices 142 and 144. Additionally, the control units 50 and 52 may be constructed so that the system does not require a separate networking computer 140. For example, the control units 50 and 52 may be constructed and/or configured to directly transmit information through the communication network 148.

The system 10 may include a second network port 150 that is coupled to a robot/device controller(s) 152 and the communication network 148. The device controller 152 controls the articulate arms 16, 18, 20, 22 and 24. The second network port 150 may be a computer that is coupled to the controller 152 by an interconnect device 154. Although an interconnect device 154 and network computer 150 are shown and described, it is to be understood that the controller 152 can be constructed and configured to eliminate the device 154 and/or computer 150.

The communication network 148 may be any type of communication system including but not limited to, the internet and other types of wide area networks (WANs), intranets, local area networks (LANs), public switched telephone networks (PSTN), integrated services digital networks (ISDN). It is preferable to establish a communication link through a fiber optic network to reduce latency in the system. Depending upon the type of communication link selected, by way of example, the information can be transmitted in accordance with the user datagram protocol/internet protocol (UDP/IP) or asynchronous transfer mode/ATM Adaptation Layer 1 (ATM/AAL1) network protocols. The computers 140 and 150 may operate in accordance with an operating system sold under the designation VxWorks by Wind River. By way of example, the computers 140 and 150 may be constructed and configured to operate with 100-base T Ethernet and/or 155 Mbps fiber ATM systems.

Figure 8:
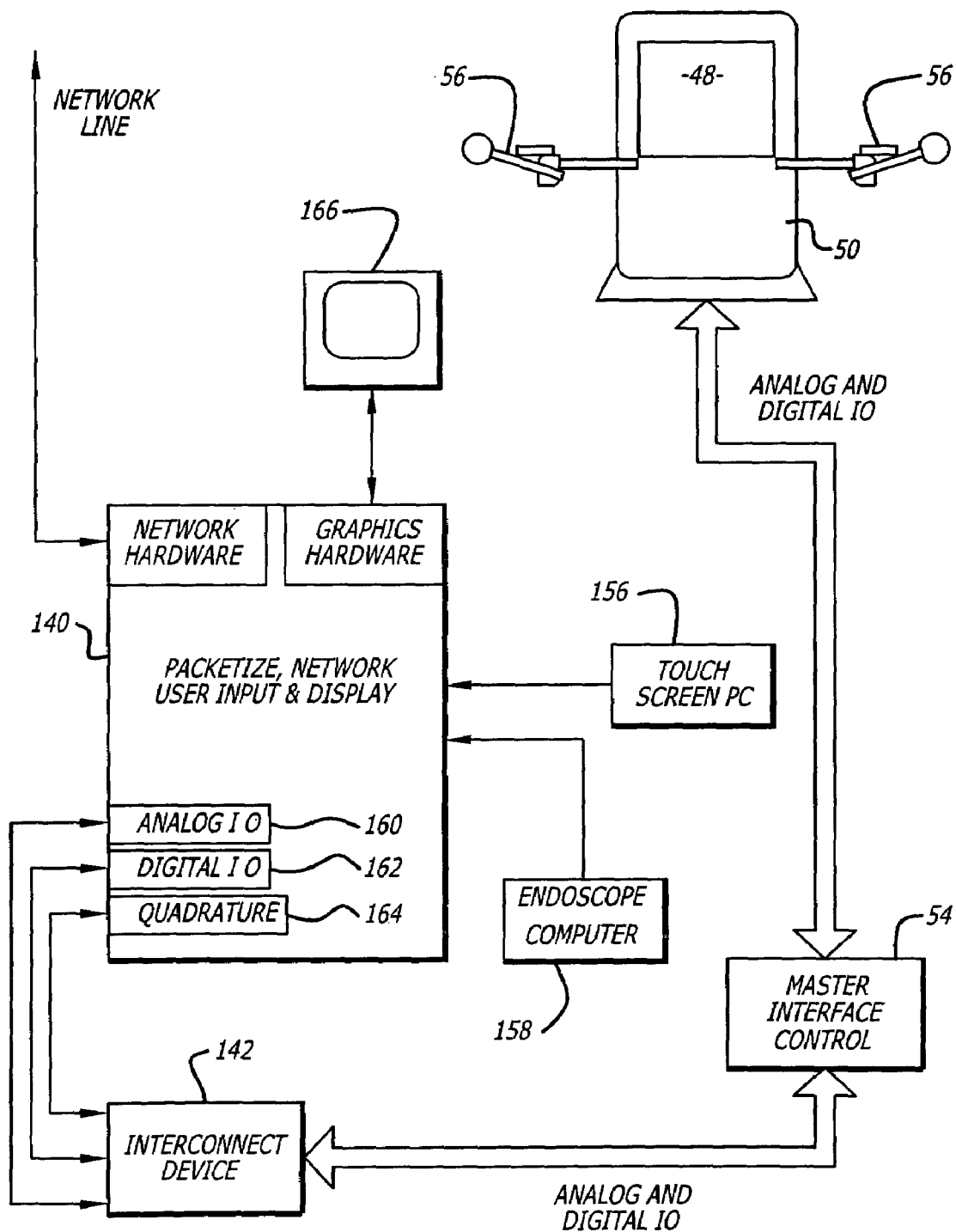
FIG. 8 is an illustration of a "surgeon" side of the network system.

FIG. 8 shows an embodiment of a mentor control unit 50. The control unit 50 may be accompanied by a touchscreen computer 156 and an endoscope interface computer 158. The touchscreen computer 156 may be a device sold by Computer Motion under the trademark HERMES. The touchscreen 156 allows the surgeon to control and vary different functions and operations of the instrument 26, 28, 30 and 32. For example, the surgeon may vary the scale between movement of the handle assemblies 56 and movement of the instruments 26, 28, 30 and 32 through a graphical user interface (GUI) of the touchscreen 156. The touchscreen 156 may have another GUI that allows the surgeon to initiate an action such as closing the gripper of an instrument.

The endoscope computer 158 may allow the surgeon to control the movement of the robotic arm 42 and the endoscope 44 shown in FIG. 1. Alternatively, the surgeon can control the endoscope through a foot pedal (not shown). The endoscope computer 158 may be a device sold by Computer Motion under the trademark SOCRATES. The touchscreen 156 and endoscope computers 158 may be coupled to the network computer 140 by RS232 interfaces or other serial interfaces.

A ZEUS control unit 50 will transmit and receive information that is communicated as analog, digital or quadrature signals. The network computer 140 may have analog input/output (I/O) 160, digital I/O 162 and quadrature 164 interfaces that allow communication between the control unit 50 and the network 148. By way of example, the analog interface 160 may transceive data relating to handle position, tilt position, in/out position and foot pedal information (if used). The quadrature signals may relate to roll and pan position data. The digital I/O interface 162 may relate to cable wire sensing data, handle buttons, illuminators (LEDs) and audio feedback (buzzers).

The position data is preferably absolute position information. By using absolute position information the robotic arms can still be moved even when some information is not successfully transmitted across the network 148. If incremental position information is provided, an error in the transmission would create a gap in the data and possibly inaccurate arm movement. The network computer 140 may further have a screen and input device (e.g. keyboard) 166 that allows for a user to operate the computer 140.

Figure 9:
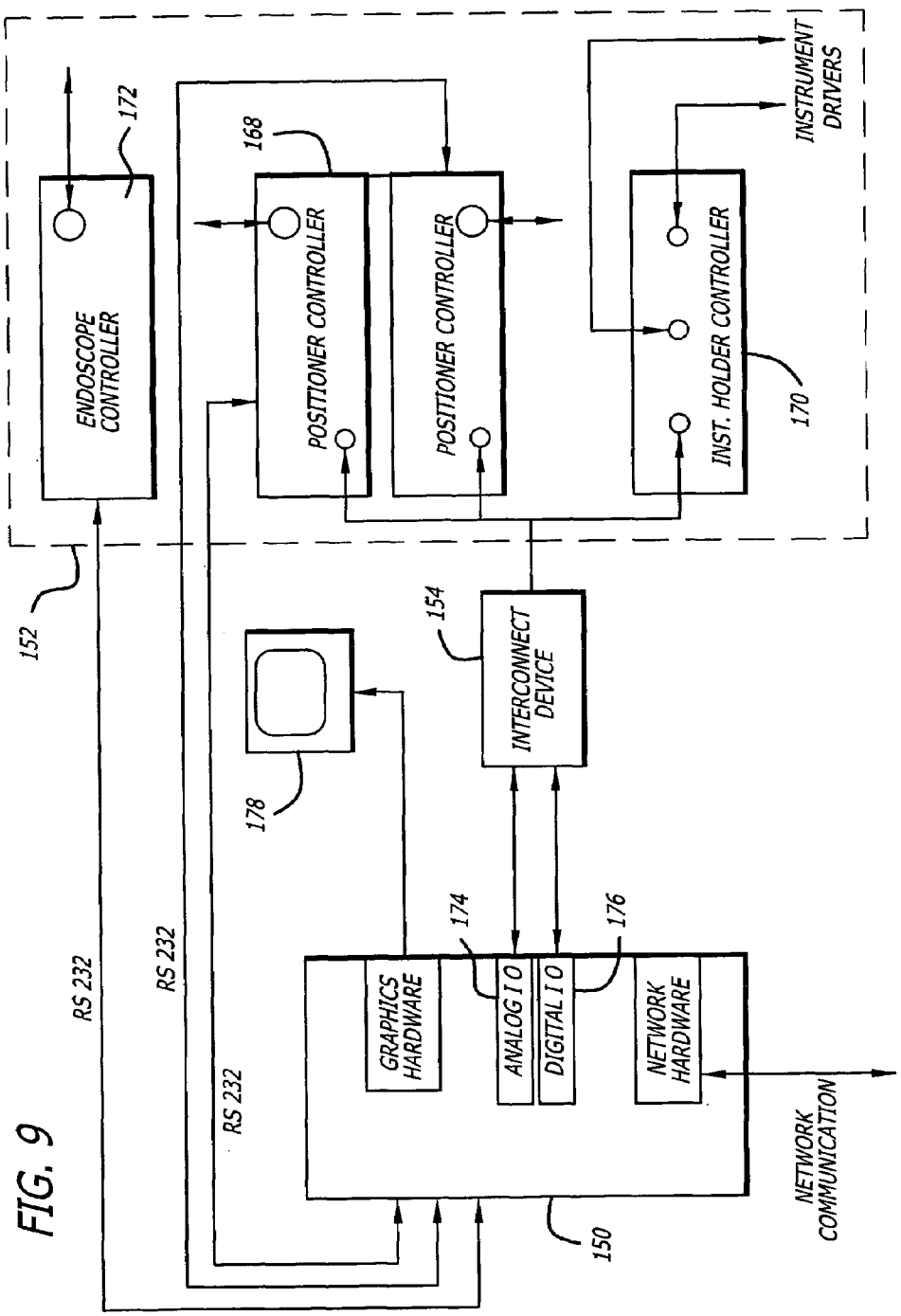
FIG. 9 is an illustration of a "patient" side of the network system.

FIG. 9 shows an embodiment of a patient side network and control computer. The controller 152 may include three separate controllers 168, 170 and 172. The controller 168 may receive input commands, perform kinematic computations based on the commands, and drive output signals to move the robotic arms 34, 36, 38 and 40 and accompanying instruments 26, 28, 30 and 32 to a desired position. The controller 170 may receive commands that are processed to both move and actuate the instruments. Controller 172 may receive input commands, perform kinematic computations based on the commands, and drive output signals to move the robotic arm 42 and accompanying endoscope 44.

Controllers 168 and 170 may be coupled to the network computer by digital I/O 176 and analog I/O 174 interfaces. The computer 150 may be coupled to the controller 172 by an RS232 interface or other serial type interfaces. Additionally, the computer 150 may be coupled to corresponding RS232 ports or other serial ports of the controller 168 and 170. The RS 232 ports or other serial ports of the controllers 168 and 170 may receive data such as movement scaling and end effector actuation.

The robotic arms and instruments contain sensors, encoders, etc. that provide feedback information including force and position data. Some or all of this feedback information may be transmitted over the network 148 to the surgeon side of the system. By way of example, the analog feedback information may include handle feedback, tilt feedback, in/out feedback and foot pedal feedback. Digital feedback may include cable sensing, buttons, illumination and auditory feedback. The computer 150 may be coupled to a screen and input device (e.g. keyboard) 178. Referring to FIG. 7, the computers 140 and 150 may packetize the information for transmission through the communication network 148. Each packet will contain two types of data, robotic data and other needed non-robotic data. Robotic data may include position information of the robots, including input commands to move the robots and position feedback from the robots. Other data may include functioning data such as instrument scaling and actuation.

Because the system transmits absolute position data the packets of robotic data can be received out of sequence. This may occur when using a UDP/IP protocol which uses a best efforts methodology. The computers 140 and 150 are constructed and configured to properly treat any "late" arriving packets with robotic data. For example, the computer 140 may sequentially transmit packets 1, 2 and 3. The computer 150 may receive the packets in the order of 1, 3 and 2. The computer 150 can disregard the second packet 2. Disregarding the packet instead of requesting a re-transmission of the data reduces the latency of the system. It is desirable to minimize latency to create a "real time" operation of the system.

It is preferable to have some information received in strict sequential order. Therefore the receiving computer will request a re-transmission of such data from the transmitting computer if the data is not errorlessly received. The data such as motion scaling and instrument actuation must be accurately transmitted and processed to insure that there is not an inadvertent command.

The computers 140 and 150 can multiplex the RS232 data from the various input sources. The computers 140 and 150 may have first-in first-out queues (FIFO) for transmitting information. Data transmitted between the computer 140 and the various components within the surgeon side of the system may be communicated through a protocol provided by Computer Motion under the name HERMES NETWORK PROTOCOL (HNP). Likewise, information may be transmitted between components on the patient side of the system in accordance with HNP.

In addition to the robotic and non-robotic data, the patient side of the system will transmit video data from the endoscope camera 46. To reduce latency in the system, the video data can be multiplexed with the robotic/other data onto the communication network. The video data may be compressed using conventional JPEG, etc., compression techniques for transmission to the surgeon side of the system.

Figure 10:
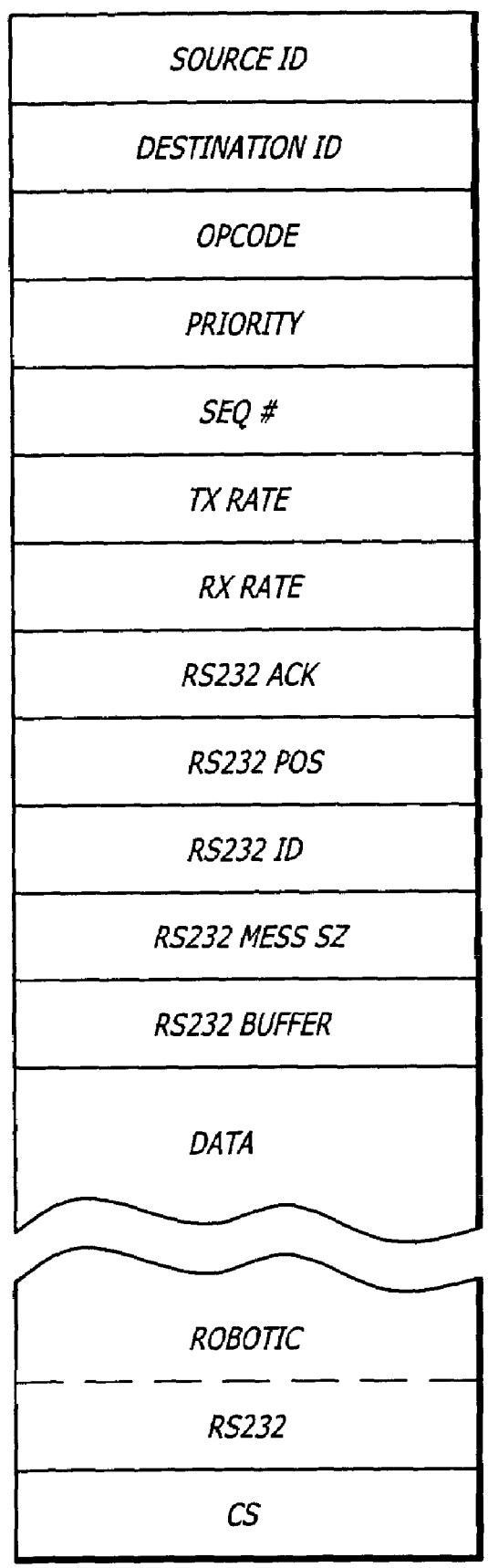
FIG. 10 is a schematic showing various fields of a packet transmitted across a communication network.

Each packet may have the fields shown in FIG. 10. The SOURCE ID field includes identification information of the input device or medical device from where the data originates. The DESTINATION ID field includes identification information identifying the input device or medical device that is to receive the data. The OPCODE field defines the type of commands being transmitted.

The PRIORITY field defines the priority of the input device. The priority data may be utilized to determine which input device has control of the medical device. The PRIORITY field may contain data that allows relative shared control of a particular instrument. For example, the mentor may have 50% control and the pupil may have 50% control.

The SEQ # field provides a packet sequence number so that the receiving computer can determine whether the packet is out of sequence. The TX Rate field is the average rate at which packets are being transmitted. The RX Rate field is the average rate that packets are being received. The RS232 or serial ACK field includes an acknowledgement count for RS232 data. RS232 data is typically maintained within the queue of a computer until an acknowledgement is received from the receiving computer that the data has been received.

The RS232 POS field is a counter relating to transmitted RS232 data. The RS232 ID field is an identification for RS232 data. The RS232 MESS SZ field contains the size of the packet. The RS232 BUFFER field contains the content length of the packet. The DATA field contains data being transmitted and may contain separate subfields for robotic and RS232 data. CS is a checksum field used to detect errors in the transmission of the packet.

Either computer 140 or 150 can be used as an arbitrator between the input devices and the medical devices. For example, the computer 150 may receive data from both control units 50 and 52. The packets of information from each control units 50 and 52 may include priority data in the PRIORITY fields. The computer 150 will route the data to the relevant device (e.g. robot, instrument, etc.) in accordance with the priority data. For example, control unit 50 may have a higher priority than control unit 52. The computer will route data to control a robot from control unit 50 to the exclusion of data from control unit 52 so that the surgeon at 50 has control of the arm.

As an alternate embodiment, the computer 150 may be constructed and configured to provide priority according to the data in the SOURCE ID field. For example, the computer 150 may be programmed to always provide priority for data that has the source ID from control unit 50. The computer 150 may have a hierarchical tree that assigns priority for a number of different input devices.

Alternatively, the computer 140 may function as the arbitrator, screening the data before transmission across the network 148. The computer 140 may have a priority scheme that always awards priority to one of the control units 50 or 52. Additionally, or alternatively, one or more of the control units 50 and/or 52 may have a mechanical and/or software switch that can be actuated to give the console priority. The switch may function as an override feature to allow a surgeon to assume control of a procedure.

In operation, the system initially performs a start-up routine. The ZEUS system is typically configured to start-up with data from the consoles. The consoles may not be in communication during the start-up routine of the robotic arms, instruments, etc. therefore the system does not have the console data required for system boot. The computer 150 may automatically drive the missing console input data to default values. The default values allow the patient side of the system to complete the start-up routine. Likewise, the computer 140 may also drive missing incoming signals from the patient side of the system to default values to allow the control units 50 and/or 52 to boot-up. Driving missing signals to a default value may be part of a network local mode. The local mode allows one or more consoles to "hot plug" into the system without shutting the system down.

Additionally, if communication between the surgeon and patient sides of the system are interrupted during operation the computer 140 will again force the missing data to the last valid or default values as appropriate. The default values may be quiescent signal values to prevent unsafe operation of the system. The components on the patient side will be left at the last known value so that the instruments and arms do not move.

Once the start-up routines have been completed and the communication link has been established the surgeons can operate the consoles. The system is quite useful for medical procedures wherein one of the surgeons is a teacher and the other surgeon is a pupil. The arbitration function of the system allows the teacher to take control of robot movement and instrument actuation at anytime during the procedure. This allows the teacher to instruct the pupil on the procedure and/or the use of a medical robotic system.

Additionally, the system may allow one surgeon to control one medical device and another surgeon to control the other device. For example, one surgeon may move the instruments 26, 28, 30 and 32 while the other surgeon moves the endoscope 44, or one surgeon may move one instrument 26, 28, 30 or 32 while the other surgeon moves the other instrument 26, 28, 30 or 32. Alternatively, one surgeon may control one arm(s), the other surgeon can control the other arm(s), and both surgeons may jointly control another arm.

Figure 11:
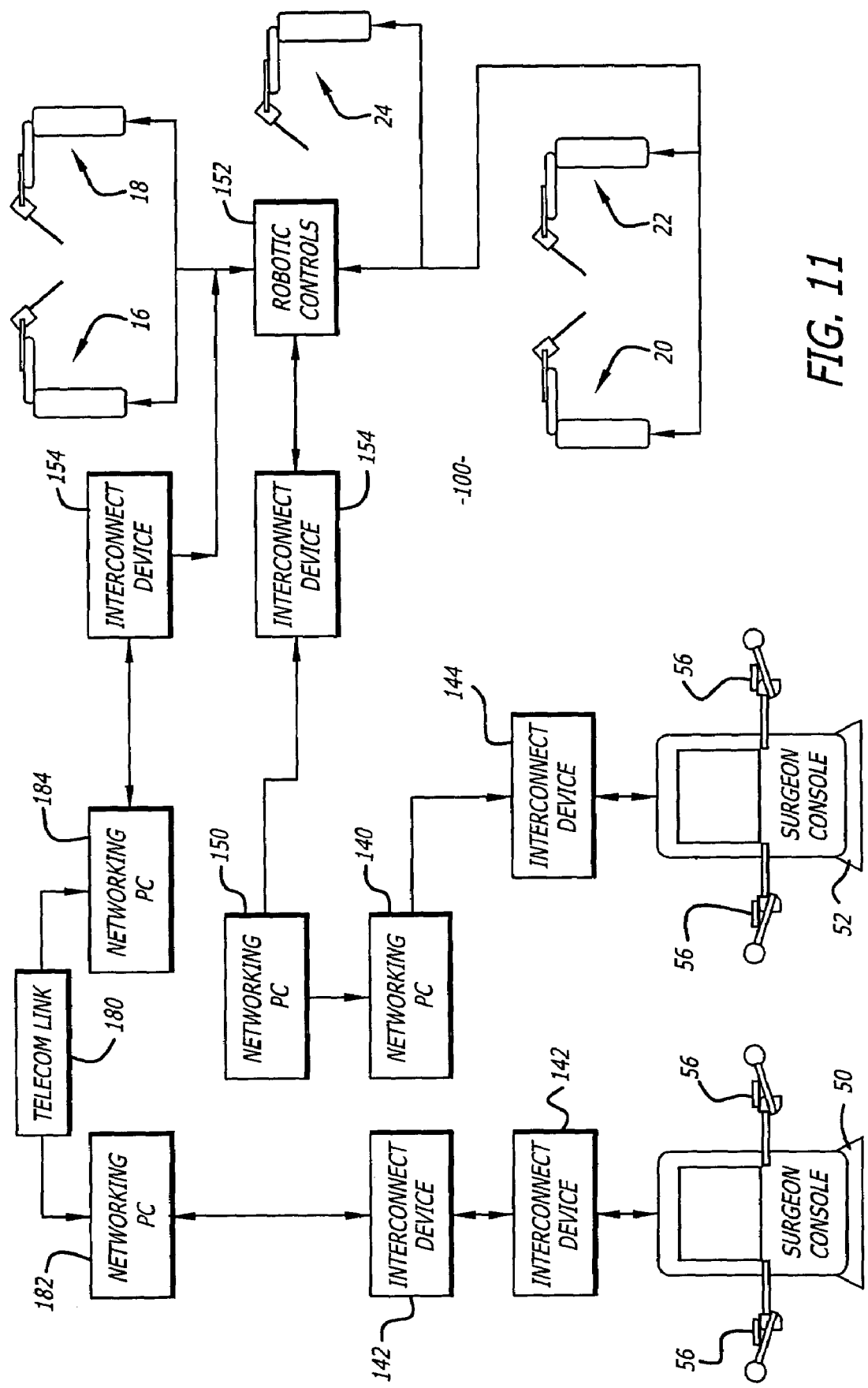
FIG. 11 is an illustration showing an alternate embodiment of the network system.

FIG. 11 shows an alternate embodiment, wherein one or more of the control units 50 and 52 has an alternate communication link 180. The alternate link may be a telecommunication network that allows the control unit 50 to be located at a remote location while control unit 52 is in relative close proximity to the robotic arms, etc. For example, control unit 50 may be connected to a public phone network, while control unit 52 is coupled to the controller 152 by a LAN. Such a system would allow telesurgery with the robotic arms, instruments, etc. The surgeon and patient sides of the system may be coupled to the link 180 by network computers 182 and 150.

Figure 12:
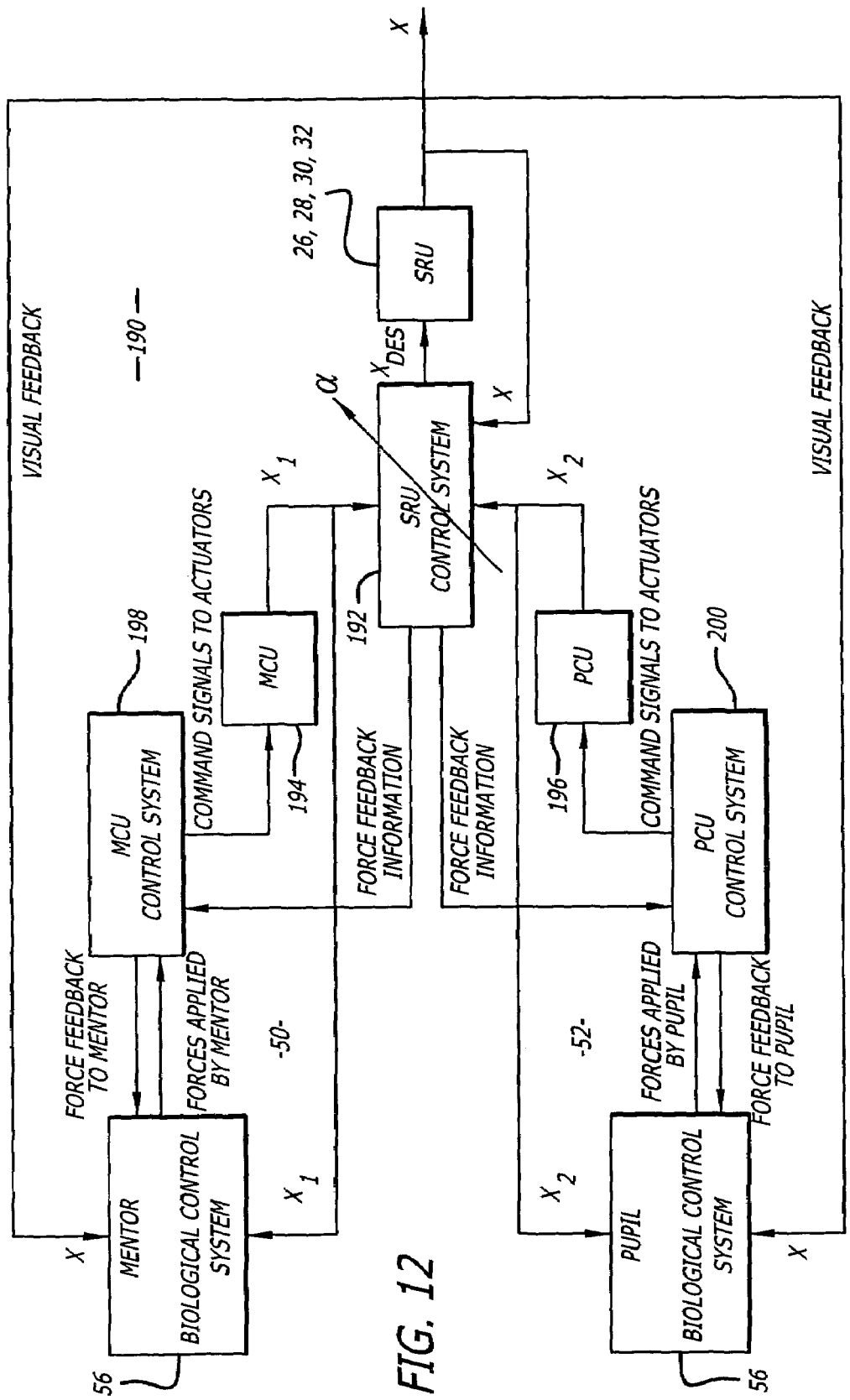
FIG. 12 is a schematic of a control system.

FIG. 12 shows a schematic of a control system 190 to allow joint control of a single medical instrument with handles from two different control units 50 and 52. The control system 190 may include an instrument controller 192 coupled to a medical instrument 26, 28, 30 and 32. The instrument controller 192 minimizes the error between the desired position $x_{des}$ of the medical instrument 26, 28, 30 or 32 and the actual position x of the instrument 26, 28, 30 or 32.

The instrument controller 192 is coupled to the position controllers 194 and 196 for the MCU 50 and PCU 52, respectively. The position controllers 194 and 196 are each connected to a corresponding handle controller 198 and 200, respectively, which is coupled to the handles 56 of each control unit. The handle controllers 198 and 200 provide output $x_1$ and $x_2$, respectively, that corresponds to the movement of the handles 56. The output is transformed to position output signals to drive the actuators of the medical instrument 26, 28, 30 or 32. The value of $x_{des}$ can be computed from x.sub.1 and x.sub.2 and a proportional control variable.

The instrument controller 192 also computes force feedback information from the force sensors of the instrument. The force feedback information is relayed back to the handle controllers 198 and 200 and handles 56 to provide force feedback to the surgeon. The amount of force feedback to each set of handles may depend on the shared control of the mentor 50 and pupil 52 control units.

Figure 13:
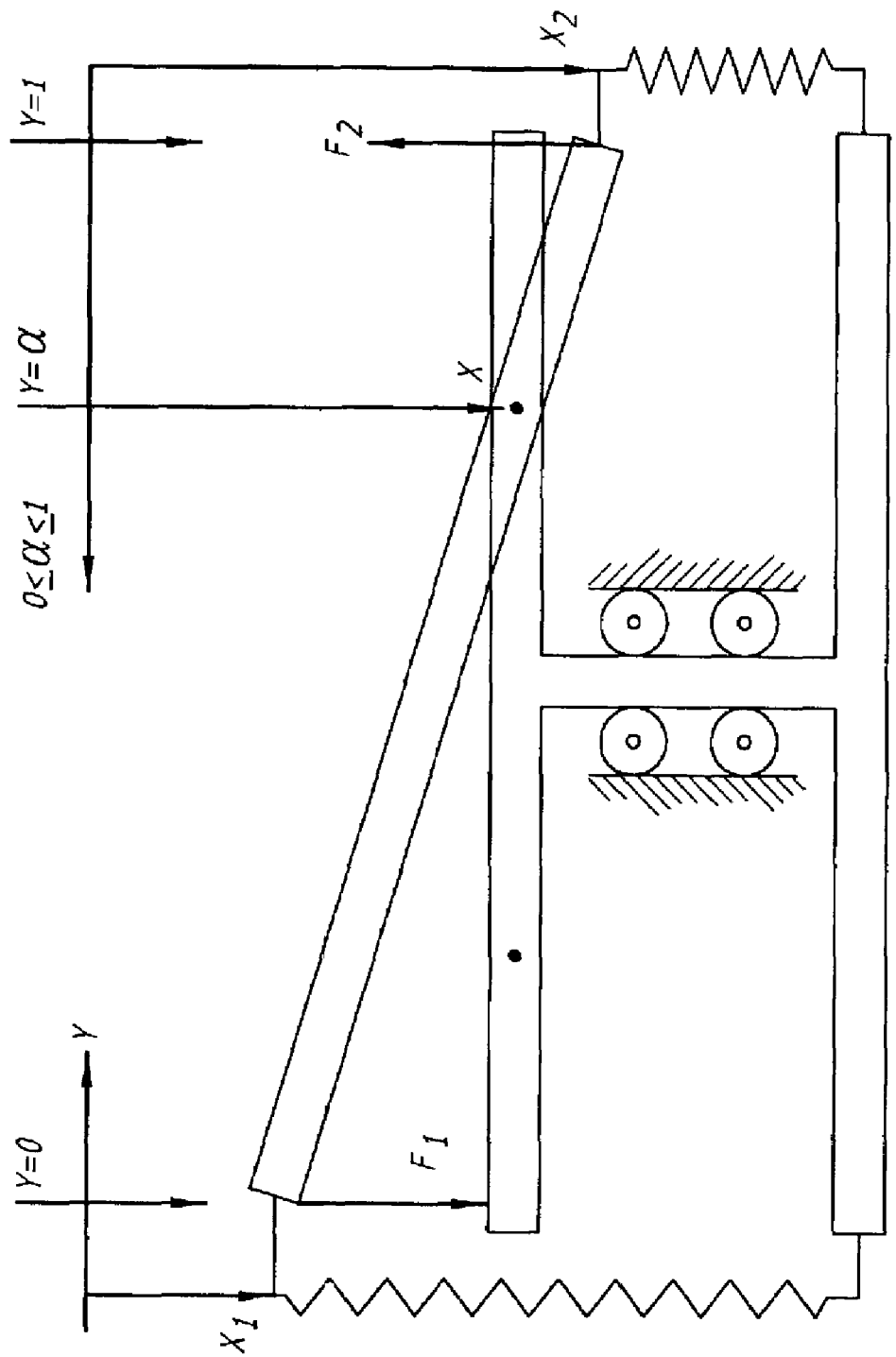
FIG. 13 is an illustration depicting collaboration between a mentor and pupil controlling a single degree of freedom instrument.

Referring to FIG. 13, the displacements of the mentor and pupil are represented by $x_1$ and $x_2$, respectively. The motion of the instrument is a convex combination of the motion of the mentor and pupil, namely, $$x=(1-\alpha)x_1+\alpha x_2 \tag{1}$$

The springs in FIG. 13 are undeformed when $x_1=x_2$, irrespective of the value of $\alpha$.

When $x_1 \neq x_2$, the deformation of the spring at the mentor end is $$x-x_1=\alpha(x_2-x_1) \tag{2}$$

The mentor therefore feels the force $$F_1=K\alpha(x_2-x_1) \tag{3}$$

Where K is the spring constant.

At the same time, the deformation of the spring at the pupil end is:

$$(x_2-x)\approx(1-\alpha)(x_2-x_1) \tag{4}$$

The pupil therefore feels the force:

$$F_2=K(1-\alpha)(x_2-x_1) \tag{5}$$

There are typically a set of equations to determine the movement x and force feedback $F_1$ and $F_2$ for each axis of each instrument. There may also be a set of equations for actuation of each end effector. For angular movement the distance is typically computed in degrees, radians or some other angular unit of measure.

When the mentor has complete control, $\alpha$ is set to 1 and the mentor handles provide no force feedback. The variable $\alpha$ can be set through the computer interfaces of the system 10. The force feedback to the pupil handles corresponds to the position information generated by the mentor handles and the position information generated by the pupil handles. Thus if the pupil handle movement deviates from the mentor handle movement, the system provides α force feedback to push the pupil into the desired hand movement. This is similar to teaching one to write with a pencil by grabbing their hand and moving the pencil. The system thus allows the mentor to guide the pupil through the motion of using the handles to move the medical instrument and perform a medical procedure. This can be a valuable instructional guide in learning how to use the system and perform robotically assisted minimally invasive procedures.

The proportional variable α allows the mentor and pupil to jointly control the movement of an instrument 26, 28, 30 and/or 32. The instrument controller 192 can compute the $x_{des}$ using equation (3). The feedback forces $F_1$ and $F_2$ are computed using equations (1) and (2) and fed back to the mentor and pupil through the force actuator for each joint.

In operation, the users may set the value of α. For example, α may be set at 0.5 for split control. Both the mentor and pupil move their handles a distance $x_1$ and $x_2$, respectively. There may in fact be multiple movements including wrist and roll movement. The controllers compute the corresponding movement x from the equation and drive the robotic arm to move the instrument. The controllers also calculate the forces $F_1$ and $F_2$ and drive the force actuators for each corresponding joint. If the pupil's and mentor's movements are in sync then the system does not provide force feedback. If the movements are out of sync the system provides a force feedback that allows the participants to "feel" the discrepancy between their movement commands.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

Although force feedback is described, it is to be understood that other means for showing pupil handle deviation may be used in the system. For example, the system may have a visual indicator such as a bar graph that indicates the deviation between the mentor and pupil handles.

What is claimed is:

1. A medical robotic system, comprising:
a first medical device;
a first input device that can be moved a first input distance to move said first medical device;
a second input device that can be moved a second input distance to move said first medical device; and,
an instrument controller programmed to generate and provide a movement command for the first medical device including a sum of first and second products wherein the first product is of the first input distance and a first factor that is proportional to the number one minus a user settable parameter value and the second product is of the second input distance and a second factor that is proportional to the user settable parameter value; generate and provide a first sensory indication so as to be sensed by a first operator of the first input device wherein the first sensory indication is proportional to a third product of the user settable parameter value and a difference between the first and second input distances; and generate and provide a second sensory indication so as to be sensed by a second operator of the second input device wherein the second sensory indication is proportional to a fourth product of the number one minus the user settable parameter value and the difference between the first and second input distances; wherein the first and second sensory indications are respectively first and second force feedbacks; and
wherein said first force feedback is applied to said first input device and said second force feedback is applied to said second input device.

2. The system of claim 1, wherein said first force feedback is generated by said instrument controller according to the following equation:

$$F_1 = K\alpha(x_2 - x_1),$$

wherein $F_1$ is the first force feedback, K is a spring constant associated with the first input device, α is a proportional variable that allows joint control of the first medical device by the first and second input devices, $x_1$ is the first input distance, and $x_2$ is the second input distance.

3. The system of claim 2, wherein the second force feedback is generated by said instrument controller according to the following equation:

$$F_2 = K(1-\alpha)(x_2 - x_1),$$

wherein $F_2$ is the second force feedback.

4. A medical robotic system, comprising:
a first medical device;
first input means that can be moved a first input distance for moving said first medical device;
second input means that can be moved a second input distance for moving said first medical device; and
controller feedback means for generating and providing a movement command for the first medical device including a sum of first and second products wherein the first product is of the first input distance and a first factor that is proportional to the number one minus a user settable parameter value and the second product is of the second input distance and a second factor that is proportional to the user settable parameter value; generating and providing a first sensory indication so as to be sensed by a first operator of the first input means wherein the first sensory indication is proportional to a third product of the user settable parameter value and a difference between the first and second input distances; and generating and providing a second sensory indication so as to be sensed by a second operator of the second input means wherein the second sensory indication is proportional to a fourth product of the number one minus the user settable parameter value and the difference between the first and second input distances; wherein the first and second sensory indications are respectively first and second force feedbacks; and wherein, said first force feedback is applied to said first input means and said second force feedback is applied to said second input means.

5. The system of claim 4, wherein said first force feedback is generated by said controller means according to the following equation:

$$F_1 = K\alpha(x_2 - x_1),$$

wherein $F_1$ is the first force feedback, K is a spring constant associated with the first input means, α is a proportional variable that allows joint control of the first medical device by the first and second input means, $x_1$ is the first input distance, and $x_2$ is the second input distance.

6. The system of claim 5, wherein the second force feedback is generated by said controller means according to the following equation:

$$F_2 = K(1-\alpha)(x_2 - x_1),$$

wherein $F_2$ is the second force feedback.

7. A method for controlling a first medical device, comprising:
- detecting movement of a first input device so as to define a first input distance;
- detecting movement of a second input device so as to define a second input distance;
- commanding a first medical device to be robotically moved according to a movement command including a sum of first and second products wherein the first product is of the first input distance and a first factor that is proportional to the number one minus a user settable parameter value and the second product is of the second input distance and a second factor that is proportional to the user settable parameter value;
- generating first and second sensory indications, wherein the first sensory indication is proportional to a third product of the user settable parameter value and a difference between the first and second input distances and the second sensory indication is proportional to a fourth product of the number one minus the user settable parameter value and the difference between the first and second input distances; and
- providing said first sensory indication so as to be capable of being sensed by a first operator operating said first input device, and providing said second sensory indication so as to be capable of being sensed by a second operator operating said second input device;
- wherein the first and second sensory indications are respectively first and second force feedbacks, and further comprising applying said first force feedback to said first input device and applying said second force feedback to said second input device.

8. The method of claim 7, further comprising:
- generating said first force feedback according to the following equation:

$$F_1 = K\alpha(x_2 - x_1),$$

wherein $F_1$ is the first force feedback, K is a spring constant associated with the first input device, $\alpha$ is a proportional variable that allows joint control of the first medical device by the first and second input devices, $x_1$ is the first input distance, and $x_2$ is the second input distance.

9. The method of claim 8, further comprising:
- generating said second force feedback according to the following equation:

$$F_2 = K(1-\alpha)(x_2 - x_1),$$

wherein $F_2$ is the second force feedback.

10. The method of claim 9, further comprising generating said movement command according to the following equation:

$$x = (1-\alpha)x_1 + \alpha x_2,$$

where x is a distance that the medical device is to be robotically moved.

* * * * *

UNITED STATES PATENT AND TRADEMARK OFFICE
CERTIFICATE OF CORRECTION

PATENT NO. : 7,413,565 B2
APPLICATION NO. : 10/948853
DATED : August 19, 2008
INVENTOR(S) : Yulun Wang et al.

Page 1 of 1

It is certified that error appears in the above-identified patent and that said Letters Patent is hereby corrected as shown below:

Title Page, Related U.S. Application Data, section (62) should read as follows:

(62) Continuation of application No. 10/051,796, filed Jan. 16, 2002, now Pat. No. 6,852,107.

In column 1, line 8, under CROSS-REFERENCES TO RELATED APPLICATIONS, the paragraph should read as follows:

The present application is a continuation of U.S. application Ser. No. 10/051,796, filed Jan. 16, 2002, now U.S. Pat. No. 6,852,107.
The full disclosure of U.S. application Ser. No. 10/246,236, filed Sep. 17, 2002, now U.S. Pat. No. 6,951,535, is incorporated herein by reference.

Signed and Sealed this
Twenty-fifth Day of September, 2012

David J. Kappos
*Director of the United States Patent and Trademark Office*